(12) United States Patent
Rosati et al.

(10) Patent No.: US 11,291,595 B2
(45) Date of Patent: Apr. 5, 2022

(54) TOPSHEET COMPRISING NATURAL FIBERS

(71) Applicant: The Procter & Gamble Company, Cincinnati, OH (US)

(72) Inventors: Rodrigo Rosati, Frankfurt am Main (DE); Gueltekin Erdem, Beijing (CN); Cornelia Sprengard-Eichel, Frankfurt (DE); Luigi Di Girolamo-Galasso, Schwalbach am Tanus (DE); Andrea Lieselotte Benner, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 792 days.

(21) Appl. No.: 16/141,086

(22) Filed: Sep. 25, 2018

(65) Prior Publication Data

US 2019/0117473 A1    Apr. 25, 2019

Related U.S. Application Data

(63) Continuation of application No. PCT/CN2017/106833, filed on Oct. 19, 2017.

(51) Int. Cl.
*A61F 13/513* (2006.01)
*A61F 13/512* (2006.01)
(Continued)

(52) U.S. Cl.
CPC .......... *A61F 13/513* (2013.01); *A61F 13/496* (2013.01); *A61F 13/512* (2013.01);
(Continued)

(58) Field of Classification Search
CPC .............. A61F 13/496; A61F 13/51104; A61F 13/51108; A61F 13/51121; A61F 13/512;
(Continued)

(56) References Cited

U.S. PATENT DOCUMENTS

| 4,324,247 A | * | 4/1982 | Aziz | .................. A61F 13/53747 604/371 |
| 4,629,643 A | * | 12/1986 | Curro | ................ A61F 13/51476 428/131 |

(Continued)

FOREIGN PATENT DOCUMENTS

| CN | 2430146 Y | 5/2001 |
| CN | 1682675 A | 10/2005 |

(Continued)

OTHER PUBLICATIONS

International Search Report and Written Opinion; Application Ser. No. PCT/CN2017/106833; dated Jun. 27, 2018, 9 pages.

(Continued)

*Primary Examiner* — Michele M Kidwell
(74) *Attorney, Agent, or Firm* — Christian M. Best

(57) ABSTRACT

A topsheet for use in an absorbent article is provided and has at least a first layer. The first layer comprises at least 15% by weight of natural fibers by total weight of the first layer. The first layer has a plurality of apertures. The first layer comprises land areas between the plurality of the apertures. The contact angle on the land areas of the first layer between the plurality of the apertures is more than 70°, according to the Contact Angle Test Method. The topsheet has a run-off of less than 40%, according to the Run-off Test Method.

19 Claims, 13 Drawing Sheets

(51) Int. Cl.
*A61F 13/511* (2006.01)
*A61F 13/496* (2006.01)
*A61F 13/515* (2006.01)
*A61F 13/51* (2006.01)

(52) U.S. Cl.
CPC ........ *A61F 13/515* (2013.01); *A61F 13/5123* (2013.01); *A61F 13/5126* (2013.01); *A61F 13/51108* (2013.01); *A61F 13/51121* (2013.01); *A61F 13/51104* (2013.01); *A61F 2013/51019* (2013.01); *A61F 2013/51033* (2013.01); *A61F 2013/51038* (2013.01); *A61F 2013/51042* (2013.01)

(58) Field of Classification Search
CPC .............. A61F 13/5123; A61F 13/5126; A61F 13/513; A61F 13/515; A61F 2013/51019; A61F 2013/51033; A61F 2013/51038; A61F 2013/51042
See application file for complete search history.

(56) References Cited

U.S. PATENT DOCUMENTS

| | | | |
|---|---|---|---|
| 4,804,378 A * | 2/1989 | Shiba | A61F 13/51305 604/367 |
| 5,273,596 A * | 12/1993 | Newkirk | A61F 13/51121 156/290 |
| 5,628,097 A * | 5/1997 | Benson | B26F 1/00 28/165 |
| 5,656,232 A | 8/1997 | Takai et al. | |
| 5,658,639 A * | 8/1997 | Curro | A61F 13/15731 428/131 |
| 6,320,096 B1 | 11/2001 | Inoue et al. | |
| 6,702,917 B1 * | 3/2004 | Venturino | A61F 13/15707 118/109 |
| 11,173,077 B2 * | 11/2021 | Erdem | A61L 15/42 |
| 2002/0064639 A1 * | 5/2002 | Rearick | B32B 5/26 428/292.1 |
| 2003/0113548 A1 | 6/2003 | Corzani et al. | |
| 2004/0127875 A1 | 7/2004 | Hammons et al. | |
| 2005/0054999 A1 | 3/2005 | Morman et al. | |
| 2005/0154362 A1 * | 7/2005 | Warren | A61L 15/34 604/367 |
| 2006/0286343 A1 * | 12/2006 | Curro | B32B 27/12 428/131 |
| 2008/0221538 A1 * | 9/2008 | Zhao | A61F 13/15707 604/367 |
| 2011/0302733 A1 * | 12/2011 | Yuan | A47K 7/03 15/104.93 |
| 2012/0321839 A1 | 12/2012 | Uematsu et al. | |
| 2014/0121625 A1 | 5/2014 | Kirby et al. | |
| 2014/0234575 A1 * | 8/2014 | Mitsuno | B32B 5/145 428/137 |
| 2014/0276512 A1 | 9/2014 | Cheng et al. | |
| 2014/0336608 A1 | 11/2014 | Hao et al. | |
| 2015/0038934 A1 * | 2/2015 | Day | A61F 13/51108 604/382 |
| 2015/0250662 A1 | 9/2015 | Isele et al. | |
| 2015/0283001 A1 | 10/2015 | Arizti et al. | |
| 2016/0074251 A1 | 3/2016 | Strube et al. | |
| 2016/0074255 A1 | 3/2016 | Strube et al. | |
| 2016/0076184 A1 * | 3/2016 | Orr | A61F 13/51104 428/178 |
| 2016/0153128 A1 | 6/2016 | Xie et al. | |
| 2017/0258646 A1 | 9/2017 | Grenier et al. | |
| 2017/0259550 A1 * | 9/2017 | Neton | A61F 13/5116 |
| 2017/0348167 A1 | 12/2017 | Tashiro et al. | |
| 2018/0051404 A1 * | 2/2018 | Novarino | D01D 5/38 |
| 2018/0177646 A1 * | 6/2018 | Burger | A61F 13/5126 |
| 2019/0053958 A1 * | 2/2019 | Kurihara | A61F 13/537 |
| 2019/0117472 A1 | 4/2019 | Erdem et al. | |
| 2019/0231612 A1 | 8/2019 | Erdem et al. | |
| 2019/0240084 A1 | 8/2019 | Rosati et al. | |
| 2020/0179177 A1 * | 6/2020 | Erdem | A61F 13/53747 |

FOREIGN PATENT DOCUMENTS

| | | | |
|---|---|---|---|
| CN | 101443499 A | 5/2009 | |
| CN | 101892557 A | 11/2010 | |
| CN | 1839776 | 4/2011 | |
| CN | 102673030 A | 9/2012 | |
| CN | 202637294 U | 1/2013 | |
| CN | 103156735 A | 6/2013 | |
| CN | 101940514 B | 12/2013 | |
| CN | 106048888 | 10/2016 | |
| CN | 106192268 | 12/2016 | |
| JP | 2005324010 A | 11/2005 | |
| JP | 2008099947 A | 5/2008 | |
| JP | 2010279621 A | 12/2010 | |
| JP | 5094992 B2 | 12/2012 | |
| JP | 2017153915 A | 9/2017 | |
| WO | 00/19949 * | 4/2000 | ............ A61F 13/15 |
| WO | 2013042501 A1 | 3/2013 | |
| WO | 2016040101 A1 | 3/2016 | |
| WO | WO2016040096 A1 | 3/2016 | |
| WO | 2017033867 A1 | 3/2017 | |

OTHER PUBLICATIONS

International Search Report and Written Opinion; Application Ser. No. PCT/CN2018/110396; dated Jan. 17, 2019, 8 pages.
All Office Actions, U.S. Appl. No. 16/141,129.
All Office Actions, U.S. Appl. No. 16/382,259.
All Office Actions, U.S. Appl. No. 16/382,273.
International Search Report and Written Opinion, PCT/CN2017/106835.

* cited by examiner

TOPSHEET COMPRISING NATURAL FIBERS

CROSS REFERENCE TO RELATED APPLICATION

This application is a continuation, under 35 USC 120, of Application No. PCT/CN2017/106833, filed on Oct. 19, 2017, which is herein incorporated by reference in its entirety.

FIELD

The invention provides a topsheet having a run-off of less than 40%, according to the Run-off Test Method described herein. The topsheet may be used in an article for personal hygiene such as a baby diaper, a training pant, a feminine hygiene sanitary napkin or an adult incontinence product.

BACKGROUND

Absorbent articles for personal hygiene, such as disposable diapers for infants, training pants for toddlers, adult incontinence undergarments and/or sanitary napkins are designed to absorb and contain body exudates, in particular large quantities of urine, runny bowel movement (BM) and/or menses. These absorbent articles may comprise several layers providing different functions, for example, a topsheet, a backsheet, and an absorbent core disposed between the topsheet and the backsheet, among other layers (e.g. acquisition layer, distribution layer, etc.) if desired.

The topsheet is generally liquid permeable and is configured to receive the fluids being excreted from the body and aid in directing the fluids toward an acquisition system, a distribution system, and/or the absorbent core. One of the important qualities of a topsheet is the ability to reduce ponding of the fluids on the topsheet before the fluids are able to be absorbed by the absorbent article.

In general, topsheets may be made to be hydrophilic via a surfactant treatment applied thereto so that the body fluids are attracted to the topsheet to then be channeled into the underlying acquisition system, distribution system, and/or absorbent core.

The topsheet may comprise natural fibers, such as cotton or bamboo fibers which are natural cellulose fibers known to have characteristics of being soft, biodegradable and less likely to cause allergies, irritations or rashes. Natural fibers are highly hydrophilic. Therefore, topsheet comprising natural fibers is typically highly hydrophilic. However, in this case, the body fluids remain on the topsheet for a long period of time resulting in a wet feel and skin discomfort for the user.

To solve the problem of the skin feeling wet during, for example, a urination event, because of prolonged fluid residency on the topsheet, the topsheet comprising natural fibers can be treated with a hydrophobic surfactant. In such case, apertured topsheets have been used to enable faster body fluids penetration. Although apertured topsheets have generally reduced fluid pendency on topsheets, topsheets with apertures have a high run-off.

Hence, there is a need to provide a topsheet for use in an absorbent article that has improved dryness characteristics while absorbing body fluids without any or few run-off.

SUMMARY

A topsheet for use in an absorbent article is disclosed, the topsheet having at least a first layer. The first layer comprises at least 15% by weight of natural fibers by total weight of the first layer. The first layer has a plurality of apertures. The first layer comprises land areas between the majority of the apertures. The contact angle on the land areas of the first layer between the majority of the apertures is more than 70°, according to the Contact Angle Test Method. The topsheet has a run-off of less than 40%, according to the Run-off Test Method.

A topsheet comprising natural fibers tends to absorb body fluids quickly and convey the body fluids through the absorbent article due to the hydrophilicity characteristics of the natural fibers. However, body fluids tend to be held in the topsheet by the natural fibers resulting in wet topsheet in contact with the wearer's skin. Therefore, the inventors have found that having a balance between the hydrophobicity of the first layer and the hydrophilicity of the natural fibers with the presence of apertures in the first layer provides a topsheet that is adequately dry and absorbs body fluids with low or no run-off. The topsheet as described above has a low run-off resulting in reducing the risk of body fluids leakage.

Moreover, the topsheet of the invention having a first layer with such value of contact angle on the land areas between the plurality of apertures allows a better absorption of body fluids. The topsheet can reduce the contact of the liquid bodily exudates with the skin of the wearer. Therefore, the topsheet is sufficiently dry when in contact with the skin of the wearer.

The first layer may comprise at least 30% by weight of natural fibers by total weight of the first layer, at least 50% by weight of natural fibers, or at least 70% by weight of natural fibers.

The natural fibers may be selected from the group consisting of cotton fibers, bamboo fibers, or a mixture thereof. The natural fibers may be cotton fibers.

The plurality of apertures may be uniformly distributed along a first surface of the first layer.

The width of the majority of the apertures may be at least 0.8 mm, or at least 1 mm, according to the Aperture Dimension Test Method. Having a first layer of the topsheet with apertures of a large width allows a better absorption of body fluids by the topsheet and compensate the hydrophobic characteristics of the first layer, i.e. the low absorption capacity layer.

On another side, the contact angle on the majority of the apertures may be less than or equal to 70°, according to the Contact Angle Test Method. The topsheet may have a drainage uptake of less than 2 g/g at 30 cm-water, according to the Capillary Drainage Test Method.

The width of the majority of the apertures may be less than 1.5 mm, less than 1 mm, or less than 0.5 mm, according to the Aperture Dimension Test Method.

By treating the apertures with hydrophilic treatment, the body fluids that are not absorb by the hydrophobic first layer are rapidly convey by the apertures toward the absorbent article's inner region. Moreover, having small width of apertures act as a barrier against the return toward the skin of body fluids that has already been absorbed by the topsheet or by the absorbent layers below the topsheet.

Therefore, the topsheet as described above provides improved fluid handling properties such as reduced rewet onto the wearer-facing surface of the absorbent article and better liquid acquisition.

The first layer may comprise a plurality of protrusions. The plurality of protrusions may impart a three-dimensional shape to the first layer. The apertures may be located between the majority of the protrusions.

Providing a three dimensional first layer of the topsheet reduces the skin/body fluids contact and/or the skin/body fluids contact time during a urination event. The skin discomfort for the wearer of the absorbent article is reduced.

The topsheet may further have a second layer in a face to face relationship with the first layer. The first layer and the second layer may be in contact with each other between the majority of the protrusions. The second layer may have a plurality of apertures at least partially aligned with the apertures of the first layer. The first layer may at least partially penetrate the second layer at the apertures. The second layer may comprise land areas between the majority of the apertures. The second layer may include synthetic fibers, natural fibers and/or combinations thereof. The synthetic fibers may be single component fibers, multi-component fibers and combinations thereof.

The second layer may be flat, or substantially flat, and the contact angle on the land areas of the second layer between the majority of the apertures may be less than or equal to 70°, according to the Contact Angle Test Method.

Alternatively, the second layer may be flat, or substantially flat, and the contact angle on the land areas of the second layer between the majority of the apertures may be more than 70°, according to the Contact Angle Test Method.

Alternatively, the second layer may comprise a plurality of protrusions. The plurality of protrusions may impart a three-dimensional shape to the second layer. The plurality of protrusions of the first layer may be at least partially aligned with the plurality of protrusions of the second layer. In this configuration, the contact angle on the land areas of the second layer between the majority of the apertures may be less than or equal to 70°, or more than 70°, according to the Contact Angle Test Method.

In these configuration, the topsheet forms a three-dimensional laminate of two layers in a face to face relationship.

When the second layer is hydrophilic (i.e. contact angle less than or equal to 70°), it improves the dewatering of the hydrophobic first layer that may be in contact with liquid bodily exudates. Therefore, when the topsheet comprising two layers is incorporated into an absorbent article, this topsheet can reduce the contact of the liquid bodily exudates with the skin of the wearer.

Moreover, when the second layer is hydrophobic (i.e. contact angle more than 70°), it reduces rewet onto the wearer-facing surface of the absorbent article.

The invention also relates to an absorbent article comprising a longitudinal centerline, a transversal centerline perpendicular to the longitudinal centerline, a topsheet as described herein, an absorbent core and a backsheet. The absorbent core is positioned at least partially intermediate the backsheet and the topsheet.

The invention also relates to a topsheet for use in an absorbent article having at least a first layer. The first layer comprises at least 80% by weight of natural fibers by total weight of the first layer. The first layer comprises from 5% to 40% by weight of hydrophilic fibers selected from the group consisting of synthetic fibers, natural fibers and/or combinations thereof, and from 60% to 95% by weight of hydrophobic natural fibers by total weight of the first layer. The topsheet has a run-off of less than 40%, according to the Run-off Test Method.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Figure 1A:
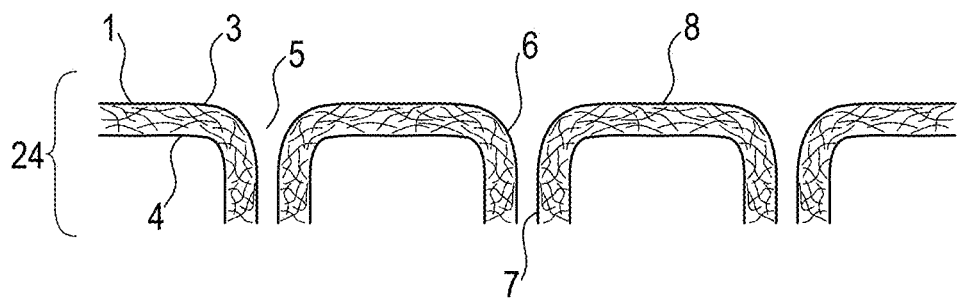
FIG. 1a is a schematic view of a topsheet having a substantially flat, or flat, first layer in accordance with the present invention.

Definition of Terms:

The term "absorbent article" as used herein refers to disposable products such as diapers, pants or feminine hygiene sanitary napkins and the like which are placed against or in proximity to the body of the wearer to absorb and contain the various liquid bodily exudates discharged from the body. Typically these absorbent articles comprise a topsheet, backsheet, an absorbent core and optionally an acquisition layer and/or distribution layer and other components, with the absorbent core normally placed between the backsheet and the acquisition system or topsheet. The absorbent article of the present invention may be a diaper or pant.

The term "diaper" as used herein refers to an absorbent article that is intended to be worn by a wearer about the lower torso to absorb and contain liquid bodily exudates discharged from the body. Diapers may be worn by infants (e.g. babies or toddlers) or adults. They may be provided with fastening elements.

The term "pant" as used herein refers to an absorbent article having fixed edges, a waist opening and leg openings designed for infant or adult wearers. A pant is placed in position on the wearer by inserting the wearer's legs into the leg openings and sliding the pant-type absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened).

The degree of hydrophilicity or hydrophobicity can be measured in each case by determining the contact angle of water with the specific material.

The term "hydrophilic" refers to a material having a contact angle of less than or equal to 70°, according to the Contact Angle Test Method described herein.

The term "hydrophobic" refers to a material having a contact angle greater than 70°, according to the Contact Angle Test Method described herein.

The term "a majority of the apertures" as used herein means that more than 50%, or more than 60%, or more than 70%, or more than 80%, or more than 90%, up to 100% of the apertures in the topsheet.

The term "bonding areas" means the areas where the first layer and the second layer of the topsheet of the present invention are joined together or are attached to each other through several methods of bonding to form a topsheet.

The term "nonwoven web" as used herein refers to a manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. The fibers may be staple or continuous filaments or be formed in situ. The porous, fibrous structure of a nonwoven may be configured to be liquid permeable or impermeable, as desired.

The term "cellulosic fiber" as used herein refers to natural fibers which typically are wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web.

The Topsheet:

The topsheet of the invention is the part of the absorbent article that is in contact with the wearer's skin. The topsheet may be joined to portions of the backsheet, the absorbent core, the barrier leg cuffs of an absorbent article, and/or any other layers as is known to those of ordinary skill in the art. The topsheet may be compliant, soft-feeling, and non-irritating to the wearer's skin. Further, at least a portion of, or all of, the topsheet may be liquid permeable, permitting liquid bodily exudates to readily penetrate through its thickness.

The topsheet of the present invention may be woven or nonwoven web of natural fibers, synthetic fibers or a combination of natural and synthetic fibers. The topsheet of the present invention may be a nonwoven web of natural fibers, synthetic fibers or a combination of natural and synthetic fibers.

Synthetic fibers may be selected from the group consisting of polyesters, polypropylenes, polyethylenes, polyethers, polyamides, polyhydroxyalkanoates, polysaccharides, and combinations thereof. More specifically, Synthetic fibers may be selected from the group consisting of polyethylene terephthalate, polybutylene terephthalate, poly(1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer, polycaprolactone, polyhydroxyl ether ester, polyhydroxyl ether amide, polyesteramide, polylactic acid, polyhydroxybutyrate, and combinations thereof. Additionally, other synthetic fibers such as rayon, polyethylene, and polypropylene fibers can be used within the scope of the present disclosure.

The synthetic fibers may be polypropylene, polyethylene, polyester, polyethylene terephthalate, polybutylene terephthalate, polyamide, polylactic acid, and/or combinations thereof.

Further, the synthetic fibers may be a single component fibers (i.e., single synthetic material or a mixture to make up the entire fiber), multicomponent fibers, such as bicomponent fibers (i.e., the fiber is divided into regions, the regions including two or more different synthetic materials or mixtures thereof), and combinations thereof.

Nonlimiting examples of suitable bicomponent fibers are fibers made of copolymers of polyester (polyethylene terephthalate/isophtalate/polyester (polyethylene terephthalate) otherwise known as "CoPET/PET" fibers, which are commercially available from Fiber Innovation Technology, Inc., Johnson City, Tenn.

The topsheet may also comprise semi-synthetic fibers made from polymers, specifically hydroxyl polymers. Nonlimiting examples of suitable hydroxyl polymers include polyvinyl alcohol, starch, starch derivatives, chitosan, chitosan derivatives, cellulose derivatives such as viscose, gums, arabinans, galactans, Lyocell (Tencel®) and combinations thereof.

Natural fibers may be selected from the group consisting of wheat straw fibers, rice straw fibers, flax fibers, bamboo fibers, cotton fibers, jute fibers, hemp fibers, sisal fibers, bagasse fibers, hesperaloe fibers, miscanthus, marine or fresh water algae/seaweeds and combinations thereof.

The natural fibers may be cotton fibers, bamboo fibers, and/or mixtures thereof.

Several examples of nonwoven materials suitable for use as a topsheet may include, but are not limited to: spunbonded nonwovens; carded nonwovens; carded air through nonwovens; spunlace nonwovens, needle punched nonwovens and nonwovens with relatively specific properties to be able to be readily deformed.

The nonwoven web can be formed from many processes, such as, for example, air laying processes, wetlaid processes, meltblowing processes, spunbonding processes, needle punching processes and carding processes. The fibers in the nonwoven web can then be bonded via spunlacing processes, hydroentangling, calendar bonding, through-air bonding and resin bonding.

One suitable nonwoven material as a topsheet may be an extensible polypropylene/polyethylene spunbonded nonwoven. One suitable nonwoven material as topsheet may be a spunbonded nonwoven comprising polypropylene and polyethylene. The fibers may comprise a blend of polypropylene and polyethylene. Alternatively, the fibers may comprise bi-component fibers, such as a sheath-core fiber with polyethylene on the sheath and polypropylene in the core of the fiber.

The topsheet may be a spunlace nonwoven.

The topsheet may have a basis weight from about 8 to about 60 gsm, from about 8 to about 50 gsm, or from about 8 to about 40 gsm.

The topsheet of the invention has at least a first layer. The first layer of the topsheet may be in direct contact with the wearer's skin.

The topsheet may be formed of a single layer or of multiple layers.

First Layer:

The first layer may be a woven or nonwoven web of natural fibers, synthetic fibers or a combination of natural and synthetic fibers. The first layer may be a nonwoven web of natural fibers, synthetic fibers, or a combination of natural and synthetic fibers.

The list of synthetic fibers and of natural fibers corresponds to the list disclosed above for the topsheet.

The nonwoven web can be formed from many processes, such as, for example, air laying processes, wetlaid processes, meltblowing processes, spunbonding processes, needle punching processes, and carding processes. The fibers in the nonwoven web can then be bonded via spunlacing processes, hydroentangling, calendar bonding, through-air bonding and resin bonding.

The first layer of the topsheet may be a spunlace nonwoven.

The synthetic fibers may be polypropylene, polyethylene, polyester, polyethylene terephthalate, polybutylene terephthalate, polyamide, polylactic acid, and/or combinations thereof.

The synthetic fibers may be single component fibers, multi-component fibers such as bicomponent fibers and combinations thereof.

The natural fibers may be cotton fibers, bamboo fibers, or mixtures thereof.

Cotton fibers are natural cellulosic fibers that have good liquid acquisition, good breathability and good softness. Therefore, having a topsheet comprising a first layer of cotton fibers improves the softness of the topsheet while improving the fluid handling properties of the topsheet.

The fibers may have any suitable deniers or denier ranges and/or fiber lengths or fiber length ranges.

The first layer comprises at least 15% by weight of natural fibers by total weight of the first layer.

The first layer may comprise at least 30% by weight of natural fibers by total weight of the first layer. The first layer may comprise at least 50% by weight of natural fibers by total weight of the first layer. The first layer may comprise at least 70% by weight of natural fibers by total weight of the first layer.

As the first layer of the topsheet may be in direct contact with the skin of the wearer of the absorbent article, having a high content of natural fibers, such as cotton fibers, in the first layer of the topsheet enables to have a soft feel for the wearer's skin as well as to increase the amount of biodegradable material in contact with the wearer's skin and to decrease the risk of allergies, irritations or rashes on the skin of the wearer.

The first layer has a plurality of apertures. The first layer comprises land areas between the majority of the apertures.

The contact angle on the land areas of the first layer between the majority of the apertures is more than 70°, according to the Contact Angle Test Method. The first layer is hydrophobic.

The contact angle on the land areas of the first layer between the majority of the apertures is more than 80°, according to the Contact Angle Test Method. The contact angle on the land areas of the first layer between the majority of the apertures may be more than 90°, according to the Contact Angle Test Method. The contact angle on the land areas of the first layer between the majority of the apertures may be more than 95° up to 130°, according to the Contact Angle Test Method.

A hydrophobic treatment may be applied to the first layer. The hydrophobic treatment may be petrochemical based or, at least to some extent, derived from natural sources. The hydrophobic treatment may be natural. The hydrophobic treatment may be selected from the group consisting of natural oil, butters or waxes and combination thereof. Some examples, but not limited to, are cotton seed oil, Coconut oil, Avocado oil, Jojoba oil, Castor-seed oil, Soybean oil, Almond oil, Lanolin, Olive oil, Sunflower seed oil, Eucalyptus oil, Shea butter, Cocoa butter, Murumuru butter, Almond butter, Avocado butter, Aloe butter, Mango butter, Beeswax, Soy wax, Candelilla wax, Rice-bran wax, Coconut wax.

The hydrophobic treatment may be used in an amount which increases as the percentage of cotton fibers that is present in the first layer increases. A range of the hydrophobic treatment may be from 0.1 gsm up to 10 gsm, or from 0.5 gsm to 4 gsm basis weight.

The hydrophobic treatment may be hydrophobic surfactants, such as silicone polymers or polyethers.

The first layer may comprise a hydrophobic treatment.

At least 60% of the total volume of the first layer of the topsheet may comprise a hydrophobic treatment. At least 70% of the total volume of the first layer of the topsheet may comprise a hydrophobic treatment.

The contact angle on the land areas of the first layer after a conditioning process may be more than 50°, according to the Post-conditioning Contact Angle Test Method. The contact angle on the land areas of the first layer after a conditioning process may be more than 60°, according to the Post-conditioning Contact Angle Test Method.

The hydrophobic treatment may be applied via kiss roll coating, spray, gravure printing, slot coating, dipping or other application processes known in the art.

The hydrophobic treatment may be applied as such or may be first dissolved in a solvent, which is then removed after application, or may be first mixed into water to form an emulsion, which is then removed after application. When the hydrophobic treatment is first mixed into water to form an emulsion, an emulsifying agent may be needed.

Alternatively, the first layer may comprise a mixture of hydrophobic natural fibers and hydrophilic natural fibers. The hydrophobic natural fibers may be hydrophilic natural fibers that are treated with a hydrophobic treatment before forming the first layer.

The amount of hydrophobic natural fibers may be higher than the amount of hydrophilic natural fibers.

For example, the first layer may comprise a mixture of from 5% to 40% by weight of hydrophilic natural fibers and from 60% to 95% by weight of hydrophobic natural fibers by total weight of the first layer.

Alternatively, the first layer may comprise a mixture of hydrophilic fibers selected from the group consisting of synthetic fibers, natural fibers and/or combinations thereof and hydrophobic natural fibers. The hydrophobic natural fibers may be hydrophilic natural fibers that are treated with a hydrophobic treatment before forming the first layer.

The amount of hydrophobic natural fibers may be higher than the amount of hydrophilic fibers.

For example, the first layer may comprise a mixture of from 5% to 40% by weight of hydrophilic fibers and from 60% to 95% by weight of hydrophobic natural fibers by total weight of the first layer.

Alternatively, naturally hydrophobic fibers may be used, such as cotton fibers not treated through scouring and/or bleaching with a hydrophobic treatment. Alternatively, hydrophobic viscose fibers may be used, as known in the art.

The first layer may have a basis weight in the range of about 8 gsm to about 50 gsm, or from about 20 gsm to about 40 gsm.

Alternatively, the first layer may be a nonwoven layer composed of a carrier web and of a web comprising natural fibers with part of the web comprising natural fibers entering the carrier web. The carrier web may be a nonwoven web.

The web comprising natural fibers may be formed on one side of the carrier web. Natural fibers of the natural fiber web may enter the fiber network of the carrier web and interlace with the fiber network. Understandably, the natural fibers may interlace with each other. The carrier web may also interlace with the web comprising natural fibers.

The carrier web may be made of different types of synthetic fibers. The carrier web may be made also of cellulosic fibers.

Synthetic fibers may be selected from the group consisting of polyesters, polypropylenes, polyethylenes, polyethers, polyamides, polyhydroxyalkanoates, polysaccharides, and combinations thereof. More specifically, Synthetic fibers may be selected from the group consisting of polyethylene terephthalate, polybutylene terephthalate, poly (1,4-cyclohexylenedimethylene terephthalate), isophthalic acid copolymers (e.g., terephthalate cyclohexylene-dimethylene isophthalate copolymer), ethylene glycol copolymers (e.g., ethylene terephthalate cyclohexylene-dimethylene copolymer, polycaprolactone, polyhydroxyl ether ester, polyhydroxyl ether amide, polyesteramide, polylactic acid, polyhydroxybutyrate, and combinations thereof. Additionally, other synthetic fibers such as rayon, polyethylene, and polypropylene fibers can be used within the scope of the present disclosure.

The synthetic fibers may be polypropylene, polyethylene, polyester, polyethylene terephthalate, polybutylene terephthalate, polyamide, polylactic acid, and/or combinations thereof.

The carrier web may comprise spunbond fibers or carded fibers. The carrier web may be a carded web or a spunbond web.

The web comprising natural fibers may comprise natural fibers that are cotton fibers, bamboo fibers, and mixtures thereof.

The web comprising natural fibers may comprise staple fibers. The natural fibers may be staple fibers.

The web comprising natural fibers may comprise cotton fibers and a small proportion of other fibers, such as rayon fiber, pulp fiber, and heat fusible fiber.

The capillary force may gradually increase from the side of the first layer where the web comprising natural fibers is formed to the center of the first layer in the thickness direction. Therefore, the first layer of the topsheet exhibits improved liquid handling properties from the web comprising natural fibers to the inside of the first layer, whereby the side where the web comprising natural fibers is formed provides a dry feel.

Moreover, since part of the web comprising natural fibers enters the carrier web, the web comprising natural fibers has enhanced mechanical strength such as tensile strength, therefore improving the mechanical strength of the topsheet.

The first layer may be a nonwoven layer comprising at least 20% by weight of natural fibers by total weight of the first layer and not more than 80% by weight of synthetic fibers by total weight of the first layer. The first layer may comprise at least 30% by weight of natural fibers by total weight of the first layer and not more than 70% by weight of synthetic fibers by total weight of the first layer.

One process to produce the first layer as described above will then be described and correspond to a hydroentanglement process. The carrier web may be formed via a through air bonding process, an air laying process, a carding process, or other known process in the art to form a nonwoven web. For example, by using a through air bonding process, a mixture of synthetic fibers may be formed into a carrier web with a carding machine and hot air at a predetermined temperature may be blown through the carrier web to fuse the fiber intersections. The carrier web may be conveyed on a wire mesh endless belt.

Separately, a web comprising natural fibers may be obtained by a carding machine for example.

The resulting web comprising natural fibers may be superimposed on the moving carrier web and water jets from a jet nozzle may be directed to the web comprising natural fibers. When the water jets strike the web, entanglement may occur in the web comprising natural fibers between the natural fibers and the constituent fibers of the carrier web. The water jets can also be directed to the carrier web or can be directed to both webs.

Alternatively, the topsheet of the present invention has at least a first layer. The first layer comprises at least 80% by weight of natural fibers by total weight of the first layer, at least 85% by weight of natural fibers by total weight of the first layer, at least 90% by weight of natural fibers by total weight of the first layer, or at least 95% by weight of natural fibers up to 100% by weight of natural fibers by total weight of the first layer.

The natural fibers may be cotton fibers and/or bamboo fibers.

The first layer comprises from 5% to 40% by weight of hydrophilic fibers selected from the group consisting of synthetic fibers, natural fibers and/or combinations thereof, and from 60% to 95% by weight of hydrophobic natural fibers by total weight of the first layer.

The hydrophobic natural fibers may be hydrophilic natural fibers that are treated with a hydrophobic treatment.

The topsheet as disclosed above has a run-off of less than 40%, according to the Run-off Test Method. This topsheet is adequately dry and absorbs body fluids with low or no run-off. The topsheet has a low run-off resulting in reducing the risk of body fluids leakage.

Structure of the First Layer:

Referring to FIG. 1a, the topsheet 24 has at least a first layer 1.

The first layer 1 may have a first surface 3 and a second surface 4. When the topsheet described herein is incorporated into an absorbent article, the first surface 3 of the first layer 1 is facing towards the body of the wearer and the second surface 4 of the first layer 1 is facing towards the backsheet.

The first layer 1 has a plurality of apertures 5. The apertures in the first layer of the topsheet play an important role to enable initial and fast fluid flow despite the hydrophobic first layer. Therefore, the first layer of the topsheet which is hydrophobic works in concert with the apertures to reduce wetness on the wearer-facing surface of the topsheet.

The plurality of apertures 5 may be uniformly distributed along the first surface 3 of the first layer 1. To ensure material stability, the smallest distance between the majority of the apertures regardless of their particular shape and width is at least 0.5 mm, or at least 1.5 mm. This distance is measured on the first surface 3 of the first layer 1 of the topsheet.

The plurality of apertures 5 may have an open area.

The first layer comprises land areas 8 between the majority of the apertures 5. The land areas 8 may be substantially flat areas. The land areas 8 may be flat areas or substantially flat areas.

The land areas 8 may fully surround the apertures 5. The land areas may together form a generally continuous grid through the first layer, while the apertures 5 may be discrete elements throughout the first layer.

The apertures may vary in shape. For example, the shape of the apertures as seen from the first surface of the first layer may be circular, elliptic, rectangular or polygonal. The apertures may have a circular shape, an elliptic shape or a polygonal shape.

The tridimensional shape of the apertures may be cylindrical (e.g. with a circular or elliptic base), prismatic (e.g. with a polygonal base) or truncated cone or pyramidal.

Figure 1B:
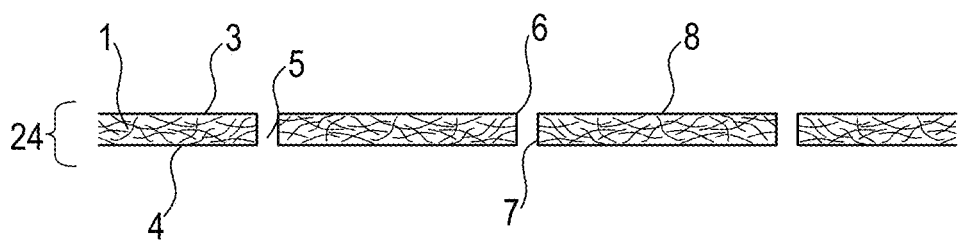
FIG. 1b is another schematic view of a topsheet having a substantially flat, or flat, first layer in accordance with the present invention.

The apertures 5 may be simply holes with no side walls, as shown in FIG. 1*b*.

Alternatively, the majority of the apertures 5 of the invention may comprise side walls that extend beyond the first surface of the first layer and extend outward of the second surface of the first layer, as shown in FIG. 1*a*.

When the topsheet described herein is incorporated into an absorbent article, the direction of the side walls of the apertures may be generally away from the absorbent core of the absorbent article or generally towards the absorbent core of the absorbent article.

The direction of the side walls of the apertures of the first layer may be towards the absorbent core of the absorbent article when the topsheet described herein is incorporated into an absorbent article.

The amount of extension of the side walls of the apertures should be at least 0.1 mm beyond the first surface of the first layer, or at least 0.2 mm beyond the first surface of the first layer. The side walls of the apertures may form funnels or channels.

The plurality of apertures 5 may comprise side walls having a top part 6 proximate to the first surface 3 of the first layer and a bottom part 7 proximate to the second surface 4 of the first layer.

Alternatively, as shown in FIG. 1*b*, the plurality of apertures 5 may be holes with a top part 6 proximate to the first surface 3 of the first layer and a bottom part 7 proximate to the second surface 4 of the first layer.

The term "top part of the apertures" means the part of the apertures that is proximate to the first surface of the first layer.

The term "bottom part of the apertures" means the part of the apertures that is proximate to the second surface of the first layer or proximate to the bottom edge of the apertures.

The plurality of apertures may also vary in width.

On one side, the contact angle on the land areas of the first layer between the majority of the apertures is more than 70°, according to the Contact Angle Test Method.

The contact angle on the first surface of the first layer between the majority of the apertures may be more than 70°, according to the Contact Angle Test Method. The contact angle on the second surface of the first layer between the majority of the apertures may be more than 70°, according to the Contact Angle Test Method.

The width of the majority of the apertures may be at least 0.8 mm, at least 1 mm, at least 1.5 mm, or at least 2 mm, according to the Aperture Dimension Test Method.

The total open area of the majority of the apertures may be in the range from 5% to 50% of the surface area of the first layer.

These large width apertures are provided to facilitate liquid transport for body fluids of various viscosities, especially feces, from the wearer facing surface towards the absorbent structure. These large width apertures compensate the hydrophobic characteristics of the first layer of the topsheet that has a low absorption capacity.

Alternatively, the contact angle on the land areas of the first layer between the majority of the apertures is more than 70°, according to the Contact Angle Test Method.

The contact angle on the first surface of the first layer between the majority of the apertures may be more than 70°, according to the Contact Angle Test Method. The contact angle on the second surface of the first layer between the majority of the apertures may be more than 70°, according to the Contact Angle Test Method.

The contact angle on the majority of the apertures may be less than or equal to 70°, according to the Contact Angle Test Method. Specifically, the contact angle on the top part and bottom part of the majority of the apertures may be less than or equal to 70°, according to the Contact Angle Test Method.

A hydrophilic treatment can be applied on the majority of the apertures. The hydrophilic treatment may be hydrophilic surfactants, such Pluronic® surfactant of BASF, Tetronic® surfactant of BASF and combinations thereof.

The majority of the apertures may comprise a hydrophilic surfactant.

The hydrophilic treatment may be applied to the majority of the apertures via the aperturing pins processes, or via printing processes, or via a hydrophilic hot melt adhesive between at least two layers of the topsheet.

For example, the aperturing pins process may correspond to a process having three rolls wherein a first roll picks up the hydrophilic surfactant from a bath and transfers it to an intermediate roll which wets the needles of the aperturing roll. Such aperturing roll needles may create the apertures in a nonwoven layer while wetting the side walls of the apertures. The excess of hydrophilic surfactant may be removed with a vacuum roller.

The apertures of the first layer of the topsheet may have at least 4% of hydrophilic open area, at least 6% of hydrophilic open area, at least 8% of hydrophilic open area.

At least 20% of the total apertures of the first layer may be hydrophilic, at least 30% of the total apertures of the first layer are hydrophilic, at least 50% of total apertures of the first layer are hydrophilic, or 100% of the total apertures are hydrophilic.

When the majority of the apertures are hydrophilic, the width of the majority of the apertures may be less than 1.5 mm, less than 1 mm, or less than 0.5 mm, according to the Aperture Dimension Test Method.

By treating the apertures with hydrophilic treatment, the body fluids that are not absorbed by the hydrophobic first layer are rapidly conveyed by the apertures toward the absorbent article's inner region. Moreover, having small width of apertures act as a barrier against the return toward the skin of body fluids that has already been absorbed by the topsheet. Furthermore, small width apertures reduce the risk of having pressure marks on the skin of the wearer.

Therefore, the topsheet as described above provides improved fluid handling properties such as a reduced rewet onto the wearer-facing surface of the absorbent article and a better liquid acquisition.

When the majority of the apertures are hydrophilic, the topsheet may have a drainage uptake of less than 2 g/g at 30 cm-water, according to the Capillary Drainage Test Method.

The topsheet may have a drainage uptake of less than 1.5 g/g at 30 cm-water, according to the Capillary Drainage Test Method. The topsheet may have a drainage uptake of less than 1 g/g at cm-water, according to the Capillary Drainage Test Method.

The topsheet having a hydrophobic first layer and hydrophilic apertures allows a rapid passage of the body fluids through its thickness toward the absorbent article's inner region.

Parameters of the Topsheet:

The topsheet of the invention may have a run-off of less than 40%, according to the Run-off Test Method. The topsheet may have a run-off of less than 20%, according to the Run-off Test Method. The topsheet may have a run-off of less than 15%, according to the Run-off Test Method.

The Run-off Test Method reproduces the in-use condition when a wearer of absorbent article discharges body fluids, such as urine or feces, on the topsheet of an absorbent article. When the run-off is high, it means that the exuded body fluids are not absorbed by the topsheet and create leakage, for example on the rear waist region of the absorbent article or on the front waist region of the absorbent article.

With the topsheet of the invention, the run-off of body fluids is low. Therefore, the risk of leakage on the rear waist region or on the front waist region of the absorbent article is reduced when the topsheet of the present invention is used in an absorbent article.

Figure 2:
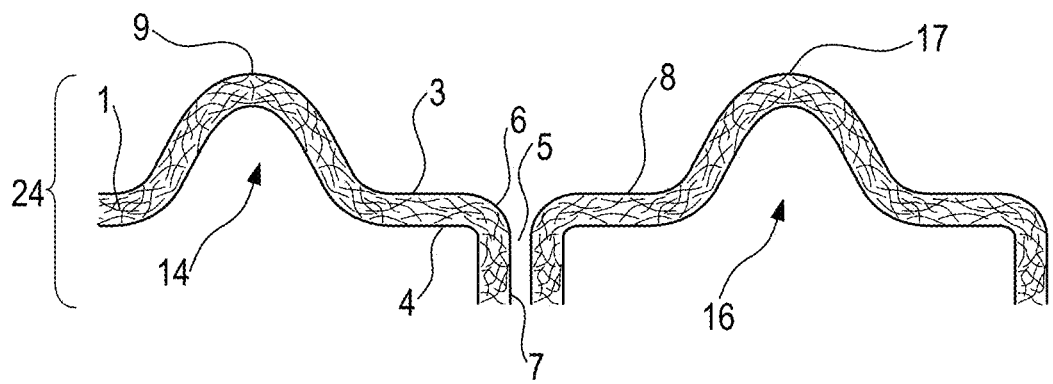
FIG. 2 is a schematic view of a topsheet having a three-dimensional first layer in accordance with the present invention.

Three-Dimensional First Layer:

According to FIG. 2, the first layer 1 may comprise a plurality of protrusions 9. The first layer 1 comprises a plurality of apertures 5. The first layer 1 comprises land areas 8 between the majority of the apertures 5 that may be substantially flat areas. The land areas 8 may be flat areas, or substantially flat areas.

The majority of the protrusions 9 may protrude from the land areas 8 of the first layer 1 of the topsheet 24 forming a base 16 and an opposed distal portion 17 from the land areas 8. The opposed distal portion 17 of the protrusions 9 may extend to a distal end which forms a top peak which is spaced away from the base of the protrusions 9. The base 16 of the majority of the protrusions 9 can be defined as the perimeter, which for circular protrusions, is the circumference, where each protrusion starts to protrude outwardly from the land areas 8 of the first layer 1.

The majority of the protrusions 9 may have a first Z-directional height.

The first layer 1 may have a first surface 3 and a second surface 4. The majority of the protrusions 9 may be located on the first surface 3 of the first layer 1. The majority of the protrusions 9 may extend outward from the first surface 3 of the first layer 1.

The plurality of the protrusions 9 may be uniformly distributed along the first surface 3 of the first layer 1. The majority of the protrusions 9 may be provided throughout the complete surface of the first layer 1 or may only be provided in a portion of the first layer 1.

The majority of the protrusions 9 may be surrounded by a plurality of land areas 8 and/or a plurality of apertures 5.

The majority of the protrusions 9 and of the land areas 8 may not be oriented in a direction parallel to the MD (Machine Direction) direction.

The plurality of protrusions 9 may impart a three-dimensional shape to the first layer 1. The plurality of land areas 8, the plurality of apertures 5 and the plurality of protrusions 9 may form a three-dimensional surface on the first surface 3 of the first layer 1 of the topsheet 24.

Alternatively, the protrusions 9 may extend outward from the second surface 4 of the first layer 1. In this case, the protrusions 9 may be named "recesses" as explained below. The plurality of land areas 8, the plurality of apertures 5 and the plurality of protrusions 9 may form a three-dimensional surface on the second surface 4 of the first layer 1 of the topsheet 24.

The majority of the protrusions 9 can be hollow.

When viewing from the first surface 3 of the first layer 1, the majority of the protrusions 9 may protrude from the land areas 8 of the first layer 1 in the same direction.

When the topsheet described herein is incorporated into an absorbent article, the plurality of protrusions may protrude away from the absorbent core of the absorbent article.

Alternatively, when the topsheet described herein is incorporated into an absorbent article, the plurality of protrusions may protrude towards the absorbent core of the absorbent article.

Viewed from a cross-sectional view, i.e. in a Z-direction, the majority of the protrusions 9 may have any suitable shapes which include, but are not limited to: cylindrical, bulbous-shaped, conical-shaped and mushroom shaped.

Viewed from above, the majority of the protrusions 9 may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions. The majority of the protrusions 9 may have a dome-shape.

The majority of the protrusions 9 may form, in conjunction, one or more graphics. Having graphics can support the caregiver's perception that the absorbent article is well able to absorb the liquid bodily exudates.

Also, the majority of the protrusions 9 may form, in conjunction, one or more graphics such as a logo, e.g. the Pampers Heart logo.

Two or more adjacent protrusions 9 may be separated by one or more land areas 8 and/or one or more apertures 5 in a direction generally perpendicular to the longitudinal axis of the first layer 1 or in a direction generally parallel to the longitudinal axis of the first layer 1.

The majority of the protrusions 9 extending outwardly from the first surface 3 of the first layer 1 may represent at least 20%, at least 30%, at least 40%, at least 50%, at least 70%, at least 80% but not more than 95% of the total area of the first layer 1 of the topsheet 24.

The majority of the protrusions 9 may have a Z-directional height in the range from about 300 μm to about 6000 μm, from about 500 μm to about 5000 μm, or from about 750 μm to about 3000 μm.

The majority of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

When the topsheet 24 described herein is incorporated into an absorbent article, the topsheet may be in close contact with underlaying layers such as a distribution layer. The underlaying layers may be made of unconsolidated dry-laid fibers of a dry-laid fibrous structure or a wet-laid fibrous structure. The void volumes 14 of the protrusions 9 can allow feces to be absorbed and acquired within them.

The majority of the protrusions 9 may be defined by a protrusion base width $WB_1$ of the base 16 forming an opening which is measured from two side walls of the inner portion at the base 16. The majority of the protrusions 9 may be defined by a width $WD_2$ of the inside void volume 14 which is the maximum interior width measured between two side walls of the inner protrusion or which is the maximum diameter of the side wall of the inner protrusion when the distal portion 17 has a substantially circular shape. The maximum interior width $WD_2$ of the void volume 14 at the opposed distal portion 17 may be greater than the protrusion base width $WB_1$ of the base 16 of the protrusions 9. The protrusion base width $WB_1$ of the base 16 of the majority of the protrusion 9 may range from 0.5 mm to 15 mm or from 0.5 mm to 10 mm or from 0.5 mm to 5 mm or from 0.5 mm to 3 mm. Measurements of the dimensions of the protrusion base width $WB_1$ of the base 16 and the width $WD_2$ of the distal portion 17 can be made on a photomicrograph.

This three-dimensional first layer of the topsheet provides better softness to the topsheet. It also helps maintain the skin of the wearer away from body fluids in the land areas as the protrusions essentially create a space between the skin of the wearer and the body fluids.

The same characteristics as disclosed above concerning the hydrophobicity of the first layer, the width of the apertures and the hydrophilicity of the apertures apply for the three-dimensional first layer of the topsheet.

Figure 3:
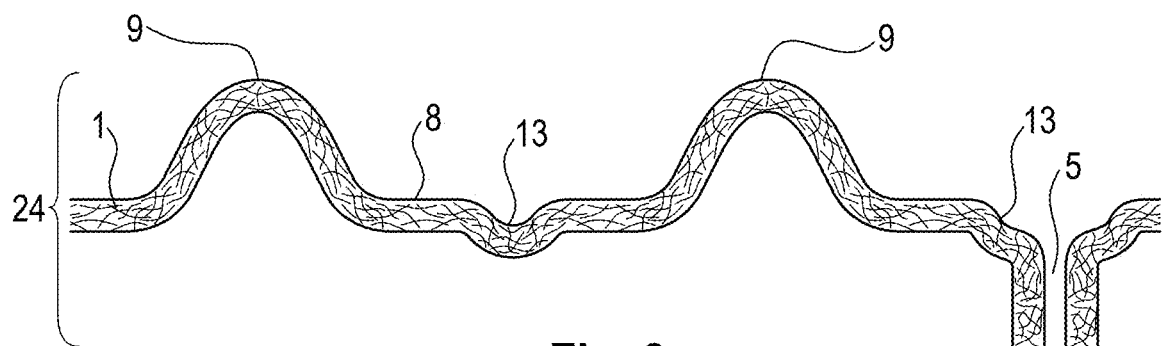
FIG. 3 is another schematic view of a topsheet having a three-dimensional first layer in accordance with the present invention.

According to FIG. 3, the first layer 1 may comprise a plurality of protrusions 9 that protrudes outward from the first surface 3 of the first layer 1 or a plurality of recesses 13 that protrudes outward from the second surface 4 of the first layer 1.

Alternatively, the first layer 1 may comprise a plurality of protrusions 9 that protrudes outward from the first surface 3 of the first layer 1 and a plurality of recesses 13 that protrudes outward from the second surface 4 of the first layer 1.

The term "recesses" corresponds to protrusions of a topsheet that protrude away from the skin of the wearer when the topsheet is incorporated into an absorbent article.

The first layer 1 may comprise a plurality of protrusions 9, a plurality of apertures 5, a plurality of recesses 13 and a plurality of land areas 8.

The plurality of land areas 8, the plurality of recesses 13, the plurality of apertures 5 and the plurality of protrusions 9 may together form a three-dimensional surface on the first side 3 of the first layer 1.

Alternatively, the first layer may comprise a plurality of recesses 13, a plurality of apertures 5 and a plurality of land areas 8. The plurality of land areas 8, the plurality of recesses 13 and the plurality of apertures 5 may together form a three-dimensional surface on the second side 4 of the first layer 1.

The plurality of recesses 13 may be separated by one or more land areas 8, one or more apertures and/or one or more protrusions 9.

The apertures 5 of the first layer may be located between the majority of the recesses 13 of the first layer 1 and/or within the majority of the recesses 13 of the first layer 1. Alternatively, some recesses 13 may not have apertures 5 therein.

The majority of the recesses 13 may define apertures 5 therein at a location most distal from the land areas 8.

The land areas 8 may be positioned intermediate to adjacent protrusions 9, adjacent recesses 13 and/or adjacent apertures 5.

The land areas 8 may form a generally continuous grid through the first layer 1 of the topsheet 24, while the protrusions 9, the apertures 5 and/or the recesses 13 may be discrete elements throughout the first layer 1 of the topsheet 24.

The majority of the recesses may have a Z-directional height in the range from about 200 μm to about 3000 μm, from about 300 μm to about 2000 μm, from about 500 μm to about 1500 μm, or from about 700 μm to about 1000 μm.

The Z-directional height of the protrusions 9 may be equal or higher than the Z-directional height of the recesses 13.

The First Layer and the Second Layer:

The topsheet may comprise a first layer and a second layer. The first layer corresponds to the first layer as described above.

The topsheet may have a second layer in a face to face relationship with the first layer as described above.

The second layer may be a woven or nonwoven web of natural fibers, synthetic fibers or a combination of natural and synthetic fibers. The second layer may be a nonwoven web of natural fibers, synthetic fibers or a combination of natural and synthetic fibers.

The list of synthetic fibers and of natural fibers corresponds to the list disclosed above for the topsheet.

The synthetic fibers may be polypropylene, polyethylene, polyester, polyethylene terephthalate, polybutylene terephthalate, polyamide, polylactic acid, and/or combinations thereof.

The synthetic fibers may be single component fibers, multi-component fibers such as bicomponent fibers and combinations thereof.

The natural fibers may be cotton fibers, bamboo fibers, and/or mixtures thereof.

The fibers may have any suitable deniers or denier ranges and/or fiber lengths or fiber length ranges.

The second layer may have a plurality of apertures. The first layer has a plurality of apertures. The second layer may have a plurality of apertures at least partially aligned with the apertures of the first layer. The apertures of the first layer may correspond to the apertures of the second layer.

The plurality of apertures of the second layer may be uniformly distributed along the first surface of the second layer.

The first layer may at least partially penetrate the second layer of the topsheet at the apertures. Alternatively, the first layer may penetrate the second layer of the topsheet at the apertures. This characteristic may be formed according to the process described below.

Alternatively, the first layer may not penetrate the second layer of the topsheet at the apertures. This characteristic may be formed by using an alternative process such as a SAN process or a hole puncher.

The plurality of apertures of the first layer and of the second layer may be simply holes with no side walls.

Alternatively, the plurality of apertures of the invention may comprise side walls that extend beyond the first surface of the first layer and extend outward of the second surface of the second layer.

When the topsheet described herein is incorporated into an absorbent article, the direction of these side walls may be generally away from the absorbent core of the absorbent article or generally towards the absorbent core of the absorbent article.

The amount of extension of the side walls of the apertures of the first layer and of the second layer should be at least 0.1 mm beyond the first surface of the first layer, or at least 0.2 mm beyond the first surface of the first layer. The side walls of the apertures of the first layer and of the second layer may form funnels or channels.

Figure 4A:
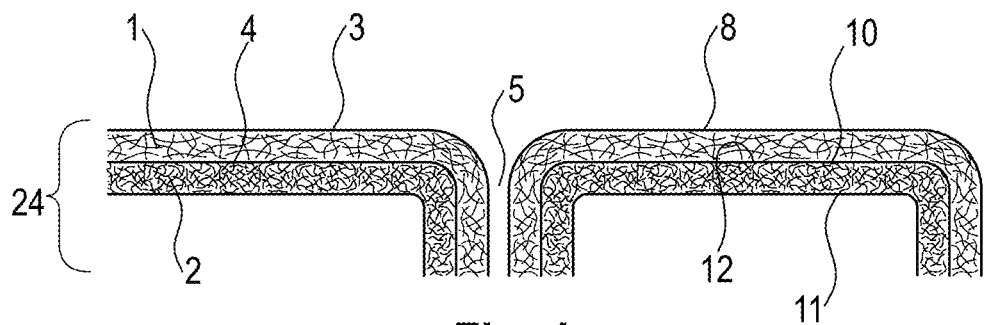
FIG. 4a is a schematic view of a topsheet having a first layer and a second layer in accordance with the present invention.

Referring to FIG. 4a, the topsheet 24 may comprise a first layer 1 and a second layer 2. The first layer may comprise a first surface 3 and a second surface 4. The second layer may comprise a first surface 10 and a second surface 11.

The first surface 10 of the second layer 2 may be in contact with the second surface 4 of the first layer 1.

When the topsheet described herein is incorporated into an absorbent article, the first surface 10 of the second layer 2 is facing towards the body of the wearer and the second surface 11 of the second layer 2 is facing towards the backsheet.

When the topsheet described herein is incorporated into an absorbent article, the first layer 1 is facing towards the body of the wearer and the second layer 2 is facing towards the backsheet.

The second layer 2 may have a plurality of apertures 5. The first layer 1 has a plurality of apertures 5. The apertures 5 may have a top part and a bottom part.

The second layer 2 may have a plurality of apertures 5 at least partially aligned with the apertures 5 of the first layer 1. The apertures 5 of the first layer 1 and of the second layer 2 may be the same. The plurality of apertures 5 of the second layer 2 may have the same width and/or length as the apertures 5 of the first layer 1.

Figure 4B:
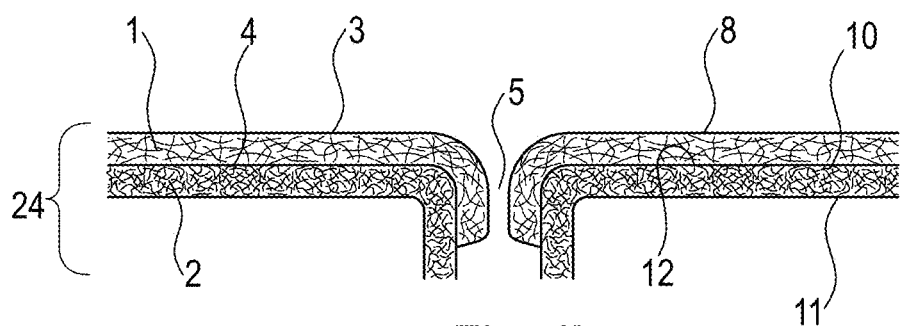
FIG. 4b is a schematic view of a topsheet having a first layer and a second layer in accordance with the present invention.

The first layer 1 may be shorter than the second layer 2 in the plurality of apertures 5, as shown in FIG. 4b. Therefore, at the bottom part of the apertures 5, the apertures 5 may be only formed by the second layer 2.

The first layer 1 comprises land areas 8 between the majority of the apertures 5. The second layer 2 may comprise land areas 12 between the majority of the apertures 5. The land areas 8 of the first layer 1 may be aligned with the land areas 12 of the second layer 2.

The land areas 8 of the first layer 1 and the land areas 12 of the second layer 2 may fully surround the apertures 5 of the first layer 1 and of the second layer 2.

The land areas 8 of the first layer 1 and the land areas 12 of the second layer 2 may be substantially flat areas. The land areas 8 of the first layer 1 and the land areas 12 of the second layer 2 may be flat areas, or substantially flat areas.

The land areas (8, 12) may together form a generally continuous grid through the first layer 1 and the second layer 2, while the apertures 5 may be discrete elements throughout the first layer 1 and the second layer 2.

The first layer 1 may be flat or substantially flat. It means that the first layer may not comprise any raised areas or protrusions.

The second layer 2 may be flat or substantially flat. It means that the second layer may not comprise any raised areas or protrusions.

The first layer and the second layer may be in contact with each other at the land areas (8, 12) and/or at the apertures 5.

The first layer and the second layer may be joined together or attached to each other through mechanical bonding, adhesive bonding, pressure bonding, heat bonding, passing heated air through both layers, or by other methods of joining to form the topsheet known in the art.

The first layer may be attached to the second layer in bonding areas by hot melt adhesive.

The bonding areas may be at the land areas (8, 12) and/or at the apertures 5.

The first layer and the second layer may be attached to each other with a hot melt adhesive applied in the form of spirals, slot coating or spray. The basis weight of the hot melt adhesive may be of at least 1 gsm, at least 5 gsm, or at least 7 gsm.

The hot melt adhesive may be hydrophilic. The hydrophilic hot melt adhesive may be selected in the group consisting of styrene block copolymers such as Styrene-Butadiene-Styrene (SBS), Styrene-Isoprene-Styrene (SIS), Styrene-Ethylene-Butadiene-Styrene (SEBS), Styrene-Ethylene-Propylene-Styrene (SEPS) and combinations thereof or other hot melt adhesive known in the art.

Having a hydrophilic hot melt adhesive attaching the first layer and the second layer can help to have a low run-off of liquid. Therefore, the risk of leakage on the rear waist region or on the front waist region of the absorbent article is reduced when the topsheet of the present invention is used in an absorbent article.

When the hot melt adhesive is applied in the land areas of the first layer and/or of the second layer, the hot melt adhesive may also reach the top and/or the side walls of the apertures.

On one side, the contact angle on the land areas of the first layer between the majority of the apertures is more than 70°, according to the Contact Angle Test Method. The contact angle on the land areas of the second layer between the majority of the apertures may be less than or equal to 70°, according to the Contact Angle Test Method.

The contact angle on the first surface of the first layer between the majority of the apertures may be more than 70°, according to the Contact Angle Test Method.

The contact angle on the second surface of the second layer between the majority of the apertures may be less than or equal to 70°, according to the Contact Angle Test Method.

The width of the majority of the apertures 5 of the first layer 1 and of the second layer 2 may be at least 0.8 mm, at least 1 mm, at least 1.5 mm, or at least 2 mm, according to the Aperture Dimension Test Method.

Alternatively, the width of the majority of the apertures 5 of the first layer 1 and of the second layer 2 may be less than 1.5 mm, less than 1 mm, or less than 0.5 mm, according to the Aperture Dimension Test Method. With these apertures having this width, the majority of the apertures 5 of the first layer 1 and of the second layer 2 may be hydrophilic.

A hydrophilic treatment can be applied on the majority of the apertures 5. The hydrophilic treatment may be hydrophilic surfactants, such Pluronic® surfactant of BASF, Tetronic® surfactant of BASF and combinations thereof.

The majority of the apertures 5 of the first layer 1 and of the second layer 2 may comprise a hydrophilic surfactant.

The hydrophilic treatment may be applied to the majority of the apertures via the aperturing pins processes as explained above, or via printing processes, or via a hydrophilic hot melt adhesive between the two layers of the topsheet.

At least 20% of the total apertures of the first layer and of the second layer may be hydrophilic, at least 30% of the total apertures of the first layer and of the second layer may be hydrophilic, or at least 50% of total apertures of the first layer and of the second layer may be hydrophilic. 100% of the total apertures of the first layer and of the second layer may be hydrophilic.

The contact angle on the majority of the apertures may be less than or equal to 70°, according to the Contact Angle Test Method. Specifically, the contact angle on the top part and bottom part of the majority of the apertures may be less than or equal to 70°, according to the Contact Angle Test Method.

On another side, the contact angle on the land areas of the first layer between the majority of the apertures is more than 70°, according to the Contact Angle Test Method. The contact angle on the land areas of the second layer between the majority of the apertures may be more than 70°, according to the Contact Angle Test Method.

A hydrophobic treatment may be applied to the second layer. The hydrophobic treatment may be chosen in the list of hydrophobic treatment disclosed above for the first layer. The second layer may comprise a hydrophobic surfactant.

At least 60% of the total volume of the second layer of the topsheet may comprise a hydrophobic surfactant. At least 70% of the total volume of the second layer of the topsheet may comprise a hydrophobic surfactant.

The hydrophobic treatment may be applied via kiss roll coating, spray, gravure printing, slot coating or other application processes, generally known to those of skill in the art.

The contact angle on the first surface of the first layer between the majority of the apertures may be more than 70°, according to the Contact Angle Test Method.

The contact angle on the second surface of the second layer between the majority of the apertures may be more than 70°, according to the Contact Angle Test Method.

The width of the majority of the apertures 5 of the first layer 1 and of the second layer 2 may be at least 0.8 mm, at least 1 mm, at least 1.5 mm, or at least 2 mm, according to the Aperture Dimension Test Method.

Alternatively, the width of the majority of the apertures 5 of the first layer 1 and of the second layer 2 may be less than 1.5 mm, less than 1 mm, or less than 0.5 mm, according to the Aperture Dimension Test Method. With the apertures having this width, the majority of the apertures may be hydrophilic as described above.

Figure 5:
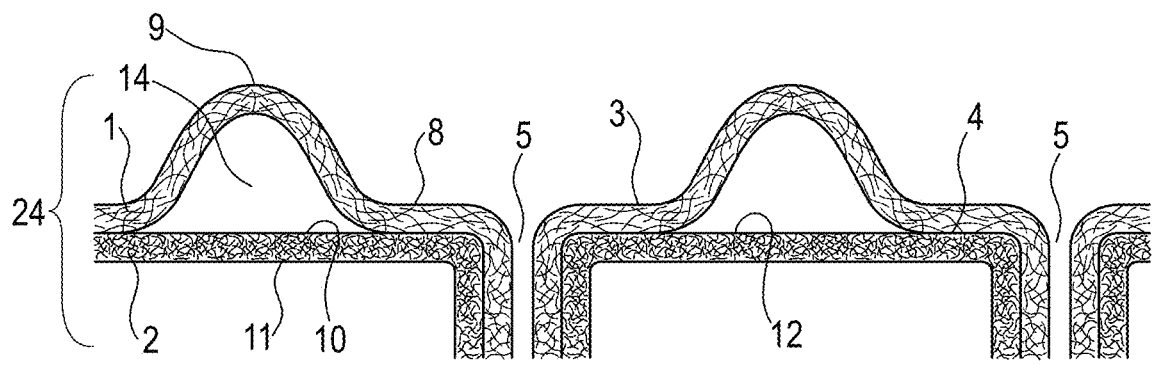
FIG. 5 is a schematic view of a topsheet having a three-dimensional first layer and a substantially flat, or flat, second layer in accordance with the present invention.

The Three-Dimensional First Layer and the Second Layer:

Referring to FIG. 5, the topsheet may comprise a three-dimensional first layer 1 and a flat, or substantially flat, second layer 2. The first layer may comprise a first surface 3 and a second surface 4. The second layer may comprise a first surface 10 and a second surface 11.

The first surface 10 of the second layer 2 may be in contact with the second surface 4 of the first layer 1.

When the topsheet described herein is incorporated into an absorbent article, the first surface 10 of the second layer 2 is facing towards the body of the wearer and the second surface 11 of the second layer 2 is facing towards the backsheet.

When the topsheet described herein is incorporated into an absorbent article, the first layer 1 is facing towards the body of the wearer and the second layer 2 is facing towards the backsheet.

The second layer 2 may have a plurality of apertures 5. The first layer 1 has a plurality of apertures 5. The apertures 5 may have a top part and a bottom part.

The second layer 2 may have a plurality of apertures 5 at least partially aligned with the apertures 5 of the first layer 1. The apertures 5 of the first layer 1 and of the second layer 2 may be the same. The plurality of apertures 5 of the second layer 2 may have at least partially the same width and/or length as the apertures 5 of the first layer 1.

The first layer 1 may be shorter than the second layer 2 in the plurality of apertures 5. Therefore, at the bottom part of the apertures 5, the apertures 5 may be only formed by the second layer 2.

The first layer 1 may have a plurality of protrusions 9. The first layer 1 comprises land areas 8 that may be substantially flat areas. The land areas 8 may be flat areas or substantially flat areas.

The majority of the protrusions 9 and of the land areas 8 may not be oriented in a direction parallel to the MD (Machine Direction) direction.

The majority of the protrusions 9 may protrude from the land areas 8 of the first layer 1 of the topsheet 24 forming a base and an opposed distal portion from the land areas 8. The opposed distal portion of the protrusions 9 may extend to a distal end which forms a top peak which is spaced away from the base of the protrusions 9.

The majority of the protrusions 9 may be located on the first surface 3 of the first layer 1. The majority of the protrusions 9 may be surrounded by a plurality of land areas 8 and/or by a plurality of apertures 5. The plurality of land areas 8, the plurality of apertures and the plurality of protrusions may impart a three-dimensional shape to the first layer 1 of the topsheet 24.

The plurality of the protrusions 9 may be uniformly distributed along the first surface 3 of the first layer 1.

The majority of the protrusions 9 can be hollow. When viewing from the first surface 3 of the first layer 1, the majority of the protrusions 9 may protrude from the land areas 8 of the first layer 1 in the same direction.

When the topsheet described herein is incorporated into an absorbent article, the plurality of protrusions may protrude away from the absorbent core of the absorbent article.

Alternatively, when the topsheet described herein is incorporated into an absorbent article, the plurality of protrusions may protrude towards the absorbent core of the absorbent article.

Viewed from a cross-sectional view, i.e. in a Z-direction, the majority of the protrusions 9 may have any suitable shapes which include, but are not limited to: cylindrical, bulbous-shaped, conical-shaped and mushroom shaped.

Viewed from above, the majority of the protrusions 9 may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions.

The majority of the protrusions 9 may form, in conjunction, one or more graphics. Having graphics can support the caregiver's perception that the absorbent article is well able to absorb the liquid bodily exudates.

Also, the majority of the protrusions 9 may form, in conjunction, one or more graphics such as a logo, e.g. the Pampers Heart logo.

The second layer 2 may comprise land areas 12 between the majority of the apertures 5. The land areas 8 of the first layer 1 may be aligned with the land areas 12 of the second layer 2.

The land areas 8 of the first layer 1 and the land areas 12 of the second layer 2 may fully surround the apertures 5 of the first layer 1 and second layer 2.

The land areas 8 of the first layer 1 and the land areas 12 of the second layer 2 may be substantially flat areas. The land areas 8 of the first layer 1 and the land areas 12 of the second layer 2 may be flat areas or substantially flat areas.

The second layer 2 may be flat or substantially flat. It means that the second layer may not comprise any raised areas or protrusions.

The first layer 1 and the second layer 2 may be in contact with each other between at least a majority of the protrusions 9 of the first layer 1. The first layer and the second layer may be in contact with each other at the land areas (8, 12) and/or at the apertures 5.

The first layer and the second layer may not be in contact in the protrusions areas.

The majority of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

The first layer and the second layer may be joined together or attached to each other through mechanical bonding, adhesive bonding, pressure bonding, heat bonding, passing heated air through both layers, or by other methods of joining to form the topsheet as known in the art.

The first layer may be attached to the second layer in bonding areas by hot melt adhesive.

The bonding areas may be at the land areas (8, 12) and/or at the apertures 5.

The first layer and the second layer may be attached to each other with a hot melt adhesive applied in the form of spirals, slot coating or spray. The basis weight of the hot melt adhesive may be of at least 1 gsm, at least 5 gsm, or at least 7 gsm.

The hot melt adhesive may be hydrophilic. The hydrophilic hot melt adhesive may be styrene block copolymers such as Styrene-Butadiene-Styrene (SBS), Styrene-Isoprene-Styrene (SIS), Styrene-Ethylene-Butadiene-Styrene (SEBS), Styrene-Ethylene-Propylene-Styrene (SEPS) and combinations thereof, or other suitable hot melt adhesive known in the art.

Having a hydrophilic hot melt adhesive attaching the first layer and the second layer can help to have a low run-off of liquid. Therefore, the risk of leakage on the rear waist region or on the front waist region of the absorbent article is reduced when the topsheet of the present invention is used in an absorbent article.

When the hot melt adhesive is applied in the land areas of the first layer and/or of the second layer, the hot melt adhesive may also reach the top and/or the side walls of the apertures.

The first layer 1 may also comprise a plurality of holes. The majority of holes may not correspond to the plurality of apertures 5.

The plurality of holes may be uniformly distributed along the first surface 3 of the first layer 1. The majority of holes may not be positioned at the areas where the apertures are located.

The width of the holes may be less than 1 mm, or less than 0.5 mmm according to the Aperture Dimension Test Method.

The plurality of holes may be hydrophilic. A hydrophilic treatment can be applied on the majority of the holes. The hydrophilic treatment may correspond to the same hydrophilic treatment as described above that may be applied on the apertures.

Having a first layer of a topsheet that has a plurality of holes and of apertures allow to have a better absorption of body fluids through the first layer of the topsheet.

The plurality of holes may be formed on the first surface of the first layer before the plurality of apertures are formed.

Thus, the first layer may be pre-apertured by forming holes along the first surface of the first layer. The holes may be hydrophilic. The pre-apertured first layer may then go through the processes disclosed below to form a plurality of apertures.

The plurality of holes may be formed via the same processes disclosed below to form the plurality of apertures.

On one side, the contact angle on the land areas of the first layer between the majority of the apertures is more than 70°, according to the Contact Angle Test Method. The contact angle on the land areas of the second layer between the majority of the apertures may be less than or equal to 70°, according to the Contact Angle Test Method.

The contact angle on the first surface of the first layer between the majority of the apertures may be more than 70°, according to the Contact Angle Test Method.

The contact angle on the second surface of the second layer between the majority of the apertures may be less than or equal to 70°, according to the Contact Angle Test Method.

The width of the majority of the apertures 5 of the first layer 1 and of the second layer 2 may be at least 0.8 mm, at least 1 mm, at least 1.5 mm, or at least 2 mm, according to the Aperture Dimension Test Method.

Alternatively, the width of the majority of the apertures 5 of the first layer 1 and of the second layer 2 may be less than 1.5 mm, less than 1 mm, less than 0.5 mm, according to the Aperture Dimension Test Method. With these apertures having this width, the majority of the apertures 5 of the first layer 1 and of the second layer 2 may be hydrophilic.

A hydrophilic treatment can be applied on the majority of the apertures 5. The hydrophilic treatment may be hydrophilic surfactants, such Pluronic® surfactant of BASF, Tetronic® surfactant of BASF and combinations thereof.

The majority of the apertures 5 of the first layer 1 and of the second layer 2 may comprise a hydrophilic surfactant.

The hydrophilic treatment may be applied to the majority of the apertures via the aperturing pins processes, or via printing processes, or via a hydrophilic hot melt adhesive between the two layers of the topsheet.

At least 20% of the total apertures of the first layer and of the second layer may be hydrophilic, at least 30% of the total apertures of the first layer and of the second layer are hydrophilic, or at least 50% of total apertures of the first layer and of the second layer are hydrophilic. 100% of the total apertures of the first layer and of the second layer may be hydrophilic.

The contact angle on the majority of the apertures may be less than or equal to 70°, according to the Contact Angle Test Method. Specifically, the contact angle on the top part and bottom part of the majority of the apertures may be less than or equal to 70°, according to the Contact Angle Test Method.

On another side, the contact angle on the land areas of the first layer between the majority of the apertures is more than 70°, according to the Contact Angle Test Method. The contact angle on the land areas of the second layer between the majority of the apertures may be more than 70°, according to the Contact Angle Test Method.

A hydrophobic treatment may be applied to the second layer. The hydrophobic treatment may be chosen in the list of hydrophobic treatment disclosed above for the first layer. The second layer may comprise a hydrophobic surfactant.

At least 60% of the total volume of the second layer of the topsheet may comprise a hydrophobic surfactant, or at least 70% of the total volume of the second layer of the topsheet may comprise a hydrophobic surfactant.

The hydrophobic treatment may be applied via kiss roll coating, spray, gravure printing, slot coating or other application processes, known in the art.

The contact angle on the first surface of the first layer between the majority of the apertures may be more than 70°, according to the Contact Angle Test Method.

The contact angle on the second surface of the second layer between the majority of the apertures may be more than 70°, according to the Contact Angle Test Method.

The width of the majority of the apertures 5 of the first layer 1 and of the second layer 2 may be at least 0.8 mm, at least 1 mm, at least 1.5 mm, or at least 2 mm, according to the Aperture Dimension Test Method.

Alternatively, the width of the majority of the apertures 5 of the first layer 1 and of the second layer 2 may be less than 1.5 mm, less than 1 mm, or less than 0.5 mm, according to the Aperture Dimension Test Method. With the apertures having this width, the majority of the apertures may be hydrophilic as described above.

Figure 6:
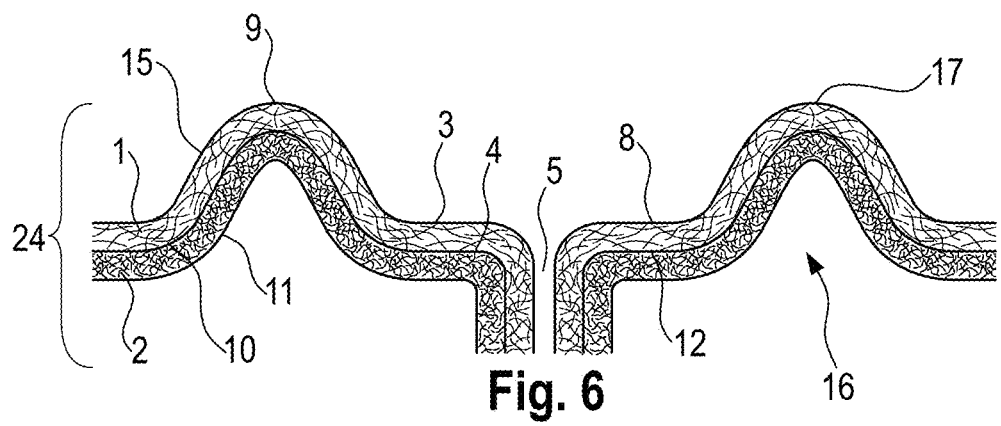
FIG. 6 is a schematic view of a three-dimensional topsheet having a first layer and a substantially flat, or flat, second layer in accordance with the present invention.

Three-Dimensional Topsheet:

Referring to FIG. 6, the topsheet 24 may be a laminate comprising the first layer 1 as previously described and a second layer 2 as previously described in a face to face relationship. In other words, the first layer 1 and the second layer 2 are joined to form a laminate.

The first layer 1 may have a first surface 3 and a second surface 4. The second layer 2 may have a first surface 10 and a second surface 11.

The first layer 1 and the second layer 2 may be aligned in a face to face relationship such that the second surface 4 of the first layer 1 is in contact with the first surface 10 of the second layer 2.

When the topsheet described herein is incorporated into an absorbent article, the first layer 1 is facing towards the body of the wearer and the second layer 2 is facing towards the backsheet.

The first layer 1 and the second layer can be simultaneously mechanically deformed and combined together to provide the topsheet having protrusions. This means that both the first layer 1 and the second layer 2 can be mechanically deformed and combined together at the same time.

The first layer 1 may comprise a plurality of protrusions 9. The second layer may comprise a plurality of protrusions 9.

The plurality of protrusions 9 of the first layer may be at least partially aligned with the plurality of protrusions 9 of the second layer 2. The protrusions 9 of the first layer 1 and of the second layer 2 may be the same.

The protrusions 9 may be at least partly formed from fibers of the first layer 1 and of the second layer 2 of the topsheet 24.

The plurality of protrusions 9 may impart a three-dimensional shape to the second layer 2. At the same time, the plurality of protrusions 9 may impart a three-dimensional shape to the first layer 1. The topsheet 24 may be a three-dimensional topsheet.

As shown in FIG. 6, the majority of the protrusions 9 may comprise a base 16 forming an opening and having a protrusion base width, an opposed distal portion 17, and one or more side walls 15 between the base 16 and the opposed distal portion 17 of the majority of the protrusions 9. The base 16, the distal portion 17 and the one or more side walls 15 may be formed by fibers such that the majority of the protrusions 9 has only opening at the base 16.

The majority of the protrusions 9 extending outwardly from the first surface 3 of the first layer 1 may represent at least 20%, at least 30%, at least 40%, at least 50%, at least 70%, at least 80% but not more than 95% of the total area of the first layer 1 of the topsheet 24.

The second layer 2 may have a plurality of apertures 5. The first layer 1 has a plurality of apertures 5. The apertures 5 may have a top part and a bottom part.

The second layer 2 may have a plurality of apertures 5 at least partially aligned with the apertures 5 of the first layer 1. The apertures 5 of the first layer 1 and of the second layer 2 may be the same. The plurality of apertures 5 of the second layer 2 may have the same width and/or length as the apertures 5 of the first layer 1.

The first layer 1 may be shorter than the second layer 2 in the plurality of apertures 5. Therefore, at the bottom part of the apertures 5, the apertures 5 may be only formed by the second layer 2.

The first layer 1 may comprise land areas 8 that may be substantially flat areas. The second layer 2 may comprise land areas 12 that may be substantially flat areas. The land areas 8 of the first layer 1 may be aligned with the land areas 12 of the second layer 2. The land areas 8 of the first layer 1 and the land areas 12 of the second layer 2 are flat areas or substantially flat areas.

The majority of the protrusions 9 may protrude from the land areas 8 of the first layer 1 and from the land areas 12 of the second layer 2.

The majority of the protrusions 9 and of the land areas 8 may not be oriented in a direction parallel to the MD (Machine Direction) direction.

The majority of the protrusions 9 may be surrounded by a plurality of land areas (8, 12) and/or by a plurality of apertures 5.

The plurality of the protrusions 9 may be uniformly distributed along the first surface 3 of the first layer 1.

The majority of the protrusions 9 can be hollow. When viewing from the first surface 3 of the first layer 1, the majority of the protrusions 9 may protrude from the land areas 8 of the first layer 1 in the same direction.

When the topsheet described herein is incorporated into an absorbent article, the plurality of protrusions may protrude away from the absorbent core of the absorbent article.

Alternatively, when the topsheet described herein is incorporated into an absorbent article, the plurality of protrusions may protrude towards the absorbent core of the absorbent article.

Viewed from a cross-sectional view, i.e. in a Z-direction, the majority of the protrusions 9 may have any suitable shapes which include, but are not limited to: cylindrical, bulbous-shaped, conical-shaped and mushroom shaped.

Viewed from above, the majority of the protrusions 9 may have any suitable shapes which include, but are not limited to: circular, diamond-shaped, round diamond-shaped, U.S. football-shaped, oval-shaped, clover-shaped, triangular-shaped, tear-drop shaped and elliptical-shaped protrusions. The majority of the protrusions 9 may have a dome-shape.

The majority of the protrusions 9 may form, in conjunction, one or more graphics. Having graphics can support the caregiver's perception that the absorbent article is well able to absorb the liquid bodily exudates.

Also, the majority of the protrusions 9 may form, in conjunction, one or more graphics such as a logo, e.g. the Pampers Heart logo.

The majority of the protrusions 9 may be made from engaging the first layer 1 with the second layer 2 such as the first layer 1 and the second layer 2 coincide with and fit together.

The first layer and the second layer may be joined together or attached to each other through mechanical bonding, adhesive bonding, pressure bonding, heat bonding, passing heated air through both layers, or by other methods of joining to form the topsheet known in the art.

The first layer may be attached to the second layer in bonding areas by hot melt adhesive.

The bonding areas may be at the land areas (8, 12), at the protrusions 9 and/or at the apertures 5.

The first layer and the second layer may be attached to each other with a hot melt adhesive applied in the form of spirals, slot coating or spray. The basis weight of the hot melt adhesive may be of at least 1 gsm, at least 5 gsm, or at least 7 gsm.

The hot melt adhesive may be hydrophilic. The hydrophilic hot melt adhesive may be styrene block copolymers such as Styrene-Butadiene-Styrene (SBS), Styrene-Isoprene-Styrene (SIS), Styrene-Ethylene-Butadiene-Styrene (SEBS), Styrene-Ethylene-Propylene-Styrene (SEPS) and combinations thereof or other hot melt adhesive known in the art.

When the hot melt adhesive is applied in the land areas of the first layer and/or of the second layer, the hot melt adhesive may also reach the top and/or the side walls of the apertures.

The majority of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

When the topsheet 24 described herein is incorporated into an absorbent article, the topsheet may be in close contact with underlaying layers such as a distribution layer. The underlaying layers may be made of unconsolidated dry-laid fibers of a dry-laid fibrous structure or a wet-laid fibrous structure. The void volumes 14 of the protrusions 9 can allow feces to be absorbed and acquired within them.

The majority of the protrusions 9 may be defined by a protrusion base width $WB_1$ of the base 16 forming an opening which is measured from two side walls of the inner portion at the base 16. The majority of the protrusions 9 may be defined by a width $WD_2$ of the inside void volume 14 which is the maximum interior width measured between two side walls of the inner protrusion or which is the maximum diameter of the side wall of the inner protrusion when the distal portion 17 has a substantially circular shape. The maximum interior width $WD_2$ of the void volume 14 at the opposed distal portion 17 may be greater than the protrusion base width $WB_1$ of the base 16 of the protrusions 9. The protrusion base width $WB_1$ of the base 16 of the majority of the protrusion 9 may range from 0.5 mm to 15 mm or from 0.5 mm to 10 mm or from 0.5 mm to 5 mm or from 0.5 mm to 3 mm. Measurements of the dimensions of the protrusion base width $WB_1$ of the base 16 and the width $WD_2$ of the distal portion 17 can be made on a photomicrograph.

The first layer 1 and the second layer 2 may comprise a plurality of protrusions 9 that protrudes outward from the first surface 3 of the first layer 1 or a plurality of recesses 13 that protrudes outward from the second surface 11 of the second layer 2.

Alternatively, the first layer 1 and the second layer 2 may comprise a plurality of protrusions 9 that protrudes outward from the first surface 3 of the first layer 1 and a plurality of recesses 13 that protrudes outward from the second surface 11 of the second layer 2.

The term "recesses" corresponds to protrusions of a topsheet that protrude away from the skin of the wearer when the topsheet is incorporated into an absorbent article.

The first layer 1 and the second layer 2 may comprise a plurality of recesses, a plurality of apertures 5, a plurality of protrusions 9 and a plurality of land areas (8,12).

Alternatively, the first layer 1 and the second layer 2 may comprise a plurality of recesses, a plurality of apertures 5 and a plurality of land areas (8,12).

The apertures 5 may be located between the majority of the recesses and/or within the majority of recesses. Some recesses may not have apertures 5 therein.

The majority of the recesses may define apertures 5 therein at a location most distal from the land areas 12.

The land areas 12 may be positioned intermediate to adjacent protrusions 9, adjacent recesses and/or adjacent apertures 5.

The plurality of recesses may be separated by one or more land areas 12, one or more apertures and/or one or more protrusions 9.

The plurality of recesses of the first layer may be aligned with the plurality of recesses of the second layer. The plurality of recesses of the first layer and of the second layer may be the same.

The first layer and the second layer may be in contact with each other at the recesses.

The majority of the recesses may have a Z-directional height in the range from about 200 µm to about 3000 µm, from about 300 µm to about 2000 µm, from about 500 µm to about 1500 µm, or from about 700 µm to about 1000 µm.

The Z-directional height of the protrusions 9 may be equal or higher than the Z-directional height of the recesses.

On one side, the contact angle on the land areas of the first layer between the majority of the apertures is more than 70°, according to the Contact Angle Test Method. The contact angle on the land areas of the second layer between the majority of the apertures may be less than or equal to 70°, according to the Contact Angle Test Method.

The contact angle on the first surface of the first layer between the majority of the apertures may be more than 70°, according to the Contact Angle Test Method.

The contact angle on the second surface of the second layer between the majority of the apertures may be less than or equal to 70°, according to the Contact Angle Test Method.

The width of the majority of the apertures 5 of the first layer 1 and of the second layer 2 may be at least 0.8 mm, at least 1 mm, at least 1.5 mm, or at least 2 mm, according to the Aperture Dimension Test Method.

Alternatively, the width of the majority of the apertures 5 of the first layer 1 and of the second layer 2 may be less than 1.5 mm, less than 1 mm, or less than 0.5 mm, according to the Aperture Dimension Test Method. With these apertures having this width, the majority of the apertures 5 of the first layer 1 and of the second layer 2 may be hydrophilic.

A hydrophilic treatment can be applied on the majority of the apertures 5. The hydrophilic treatment may be hydrophilic surfactants, such Pluronic® surfactant of BASF, Tetronic® surfactant of BASF and combinations thereof.

The majority of the apertures 5 of the first layer 1 and of the second layer 2 may comprise a hydrophilic surfactant.

The hydrophilic treatment may be applied to the majority of the apertures via the aperturing pins processes as explained above, or via printing processes, or via a hydrophilic hot melt adhesive between the two layers of the topsheet.

At least 40% of the total apertures of the first layer and of the second layer may be hydrophilic, at least 50% of the total apertures of the first layer and of the second layer may be hydrophilic, or at least 60% of total apertures of the first layer and of the second layer may be hydrophilic. 100% of the total apertures of the first layer and of the second layer may be hydrophilic.

The contact angle on the majority of the apertures may be less than or equal to 70°, according to the Contact Angle Test Method. Specifically, the contact angle on the top part and bottom part of the majority of the apertures may be less than or equal to 70°, according to the Contact Angle Test Method.

On another side, the contact angle on the land areas of the first layer between the majority of the apertures is more than 70°, according to the Contact Angle Test Method. The contact angle on the land areas of the second layer between the majority of the apertures may be more than 70°, according to the Contact Angle Test Method.

A hydrophobic treatment may be applied to the second layer. The hydrophobic treatment may be chosen in the list of hydrophobic treatment disclosed above for the first layer. The second layer may comprise a hydrophobic surfactant.

At least 60% of the total volume of the second layer of the topsheet may comprise a hydrophobic surfactant or at least 70% of the total volume of the second layer of the topsheet may comprise a hydrophobic surfactant.

The hydrophobic treatment may be applied via kiss roll coating, spray, gravure printing, slot coating or other application processes, known in the art.

The contact angle on the first surface of the first layer between the majority of the apertures may be more than 70°, according to the Contact Angle Test Method.

The contact angle on the second surface of the second layer between the majority of the apertures may be more than 70°, according to the Contact Angle Test Method.

The width of the majority of the apertures 5 of the first layer 1 and of the second layer 2 may be at least 0.8 mm, at least 1 mm, at least 1.5 mm, or at least 2 mm, according to the Aperture Dimension Test Method.

Alternatively, the width of the majority of the apertures 5 of the first layer 1 and of the second layer 2 may be less than 1.5 mm, less than 1 mm, or less than 0.5 mm, according to the Aperture Dimension Test Method. With the apertures having this width, the majority of the apertures may be hydrophilic as described above.

The Mechanical Deformations, the Resulting Protrusions and the Apertures:

A plurality of different methods known in the art may be used to create an apertured nonwoven, i.e. an apertured topsheet of the present disclosure, and to create a three-dimensional nonwoven material with apertures. These methods have been described in the PCT application WO2017/156200, published on the 14 Sep. 2017 and filed by the Procter and Gamble Company, incorporated herein by reference.

The three-dimensional, apertured, first layer of the topsheet of the present disclosure or the laminate of the first layer and the second layer of the topsheet of the present disclosure may be also industrially produced at high speed as described below.

Figure 7:
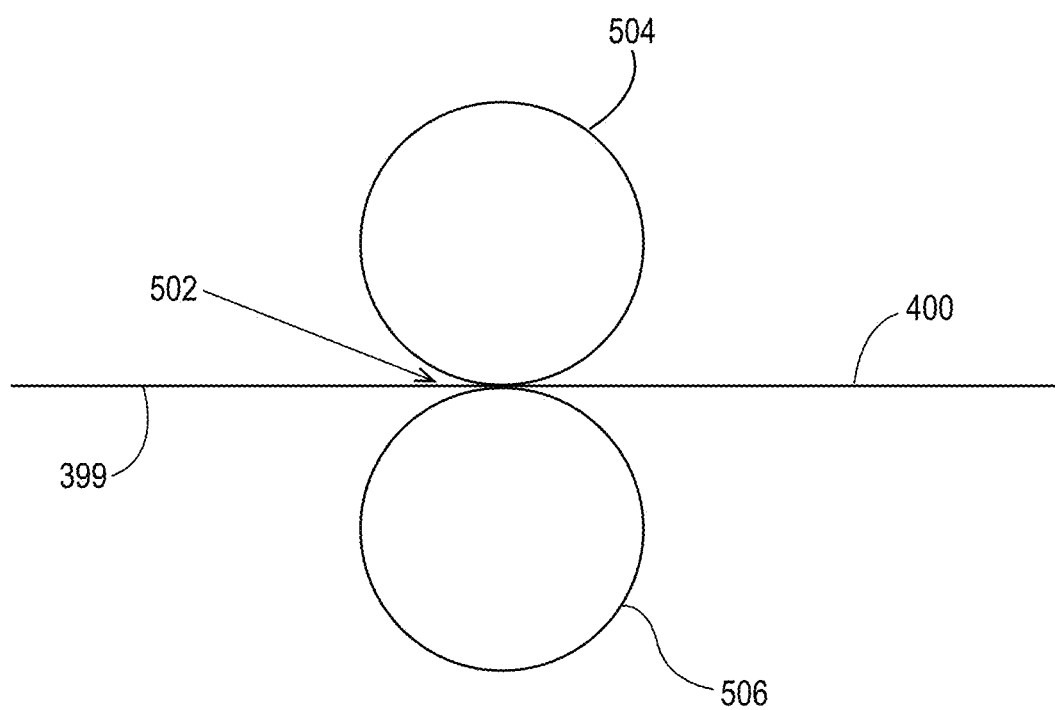
FIG. 7 is a schematic illustration of a first example process for forming the topsheet of the present disclosure.
Figure 8:
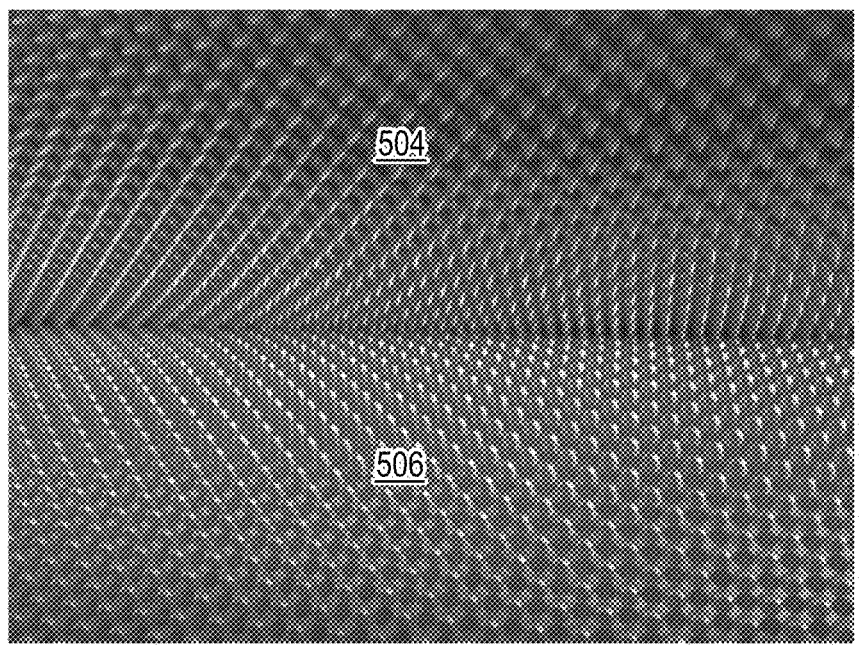
FIG. 8 is a view of intermeshing engagement of portions of first and second rolls in accordance with the present disclosure.
Figure 9:
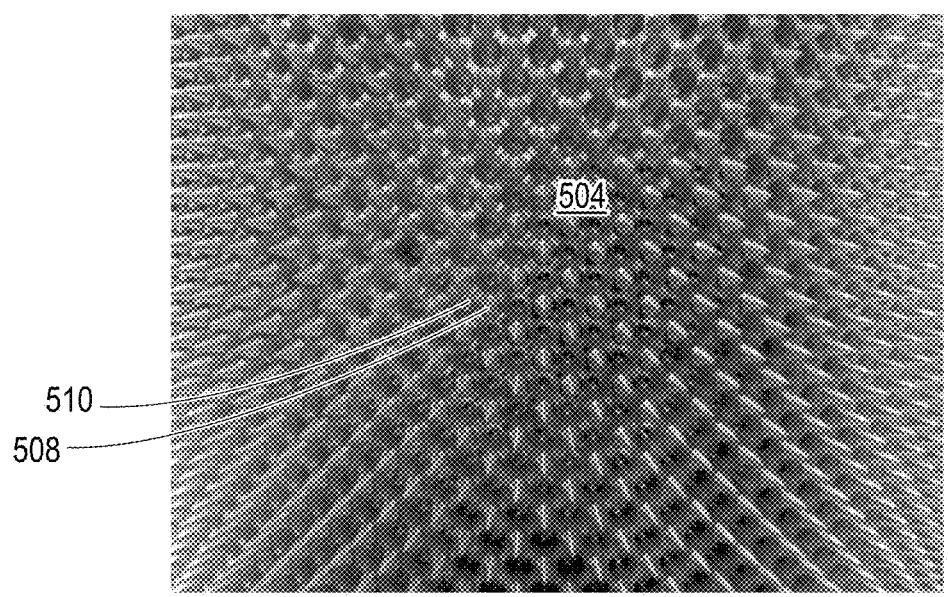
FIG. 9 is a view of a portion of the first roll in accordance with the present disclosure.
Figure 10:
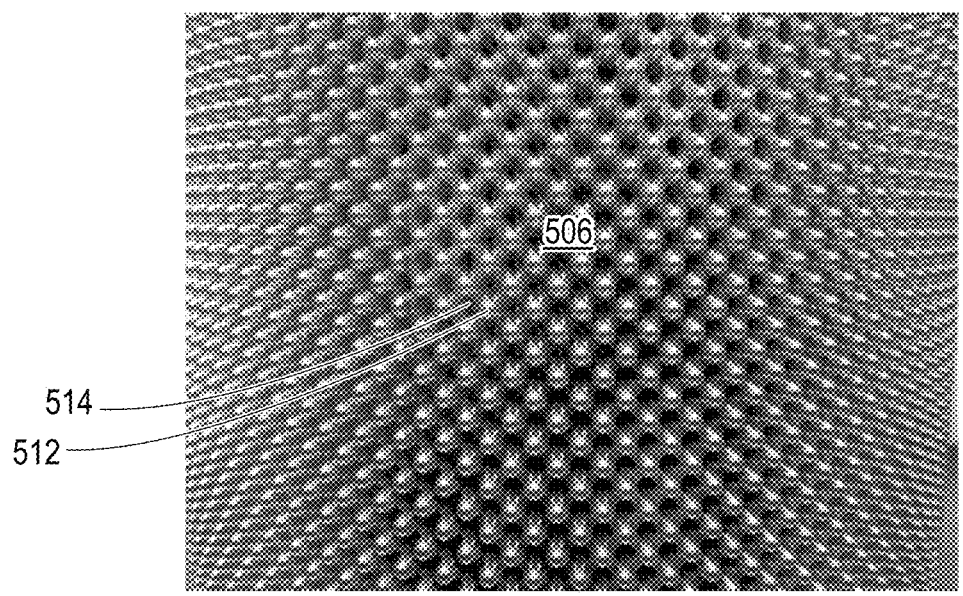
FIG. 10 is a view of a portion of the second roll in accordance with the present disclosure.

FIG. 7 is a schematic illustration of one example process for forming the substrates of the present disclosure. FIG. 8 is a view of intermeshing engagement of portions of first and second rolls. FIG. 9 is a view of a portion of the first roll. FIG. 10 is a view of a portion of the second roll.

Referring to FIGS. 7-10, the first layer of the topsheet of the present disclosure may be formed by passing one or more layer substrate 399 (non-three dimensional) through a nip 502 formed by two intermeshing rolls 504 and 506 to form a three-dimensional substrate 400. The rolls 504 and 506 may be heated. A first roll 504 may create the apertures in the substrate 400 (in combination with the second roll) and a second roll 506 may create the protrusions in the substrate 400 (in combination with the first roll). The first roll 504 may comprise a plurality of protrusions 508 extending radially outwardly from the first roll 504. The first roll 504 may also comprise a plurality of recesses 510 formed in a radial outer surface of the first roll 504. The second roll 506 may comprise a plurality of protrusions 512 extending radially outwardly from the second roll 506. The second roll 506 may also comprise a plurality of recesses 514 formed in the radial outer surface of the second roll 506. The protrusions 508 on the first roll 504 may have a different size, shape, height, area, width and/or dimension than the protrusions 512 on the second roll 506. The recesses 510 formed in the first roll 504 may have a different size, shape, height, area, width, and/or dimension than the recesses 514 formed in the second roll 506. The recesses 510 in the first roll 504 may be configured to at least partially receive the protrusions 512, thereby creating the protrusions in the substrate 400. Specifically, as the protrusions 512 engage into the recesses 510, there is sufficient depth left in the space between the surfaces in a radial direction so that the thickness of the substrate in the protrusions is higher than the thickness of the recesses. This feature provides protrusions with a softer feel and a greater height compared to compressing the portions of the substrate forming the protrusions. The recesses 514 in the second roll 506 may be configured to at least partially receive the protrusions 508 thereby creating the apertures in the first layer of the topsheet.

Alternatively, another method may be used to form the three-dimensional, apertured, first layer of the topsheet of the present disclosure or the laminate of the first and second layer of the topsheet of the present disclosure.

Figure 11:
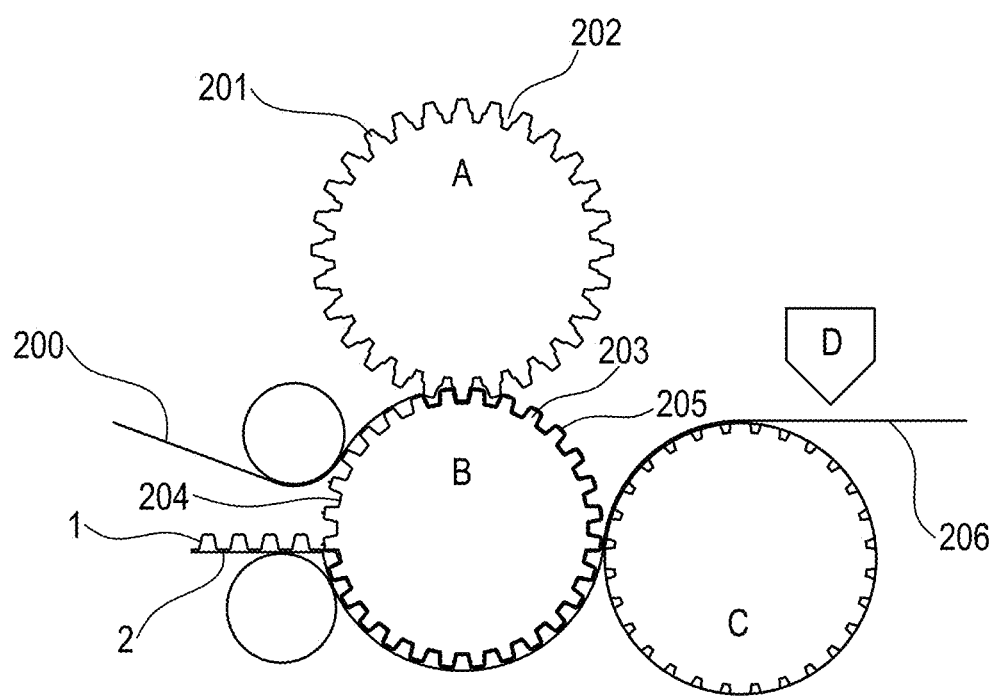
FIG. 11 is a schematic illustration of a second example process for forming the topsheet of the present disclosure.

Referring to FIG. 11, a first substrate 200 may go through a pair of rolls named A and B in order to form the first layer 1 of the present invention. The speed of the roll A and B may be from 5 to 600 meters/minute. The temperature range of the roll A may be from 40 to 200° C. The temperature range of the roll B may be from 30 to 200° C. The roll A may comprise a plurality of protrusions 201 extending radially outwardly from the roll A. The roll A may also comprise a plurality of recesses 202 formed in a radial outer surface of the roll A. The depth of the recesses 202 of the roll A may be from 0.5 to 10 mm, the depth of the protrusions 201 of the roll A may be from 0.5 to 9 mm. The roll B may comprise a plurality of protrusions 203 extending radially outwardly from the roll B. The roll B may also comprise a plurality of recesses 204 formed in a radial outer surface of the roll B. The distal end of the plurality of protrusions 203 of the roll B may have the shape of a pin 205.

The protrusions 201 on the roll A may have a different size, shape, height, area, width and/or dimension than the protrusions 203 on the roll B. The recesses 202 formed in the roll A may have a different size, shape, height, area, width, and/or dimension than the recesses 204 formed in the roll B. The recesses 202 in the roll A may be configured to at least partially receive the protrusions 203 of the roll B, thereby creating the protrusions in the first substrate 200. The roll A may comprise a plurality of holes in the recesses area in order to receive the shape of pin 205 of the protrusions 203 of the roll B. Therefore, a plurality of apertures 5 are formed in the first substrate 200 between each protrusions of the first substrate 200. The first substrate 200, after going through the roll A and the roll B may comprise a plurality of protrusions 9 and a plurality of apertures 5 between each protrusions.

A second substrate 206 may be brought by a concave roller C. Hot melt adhesive may be added on the first surface of the second substrate 206 by an equipment D before the second substrate 206 is in contact with the first substrate 200. The roll C may comprise a plurality of holes in order to receive the shape of pin 205 of the protrusions 203 of the roll B.

The second substrate 206 may pass through the roll C and the roll B and may be in contact with the first substrate 200 at the protrusions 203 of the roll B. As the protrusions 203 of the roll B may have the shape of a pin, a plurality of apertures may be created also on the second substrate 206. The plurality of apertures 5 of the second substrate 206 may be at least partially aligned with the apertures 5 of the first substrate 200.

At the end of the process, a three-dimensional, apertured first layer 1 may be obtained and may be in contact with a second layer 2 between the majority of the protrusions 9 of the first layer.

The first substrate 200 may also be the first layer 1 and the second layer 2 engaged together between the rolls A and B, simultaneously mechanically deformed and combined together to form the three-dimensional topsheet 24 of the invention.

In order to form a first layer of a topsheet with a plurality of protrusions, the first layer 1 may also be engaged between a first and second forming members and be mechanically deformed to form a first layer with a three-dimensional shape. This method has been described in the PCT application WO2017/156203, published on the 14 Sep. 2017 and filed by the Procter and Gamble Company, incorporated herein by reference. The first layer may comprise thus deformations forming protrusions 9.

Alternatively, in order to form a three-dimensional topsheet 24 having a first layer 1 and a second layer 2, the first layer 1 and the second layer 2 may be engaged together between a first and second forming members and be simultaneously mechanically deformed and combined together to form the topsheet 24. This method has been described in the PCT application WO2017/156203, published on the 14 Sep. 2017 and filed by the Procter and Gamble Company, incorporated herein by reference.

Absorbent Articles:

A typical disposable absorbent article, in which the topsheet of the present invention can be used, is placed against or in proximity to the body of the wearer to absorb and contain the various exudates discharged from the body and is represented in FIG. 12 to FIG. 16 in the form of a diaper 20.

Figure 12:
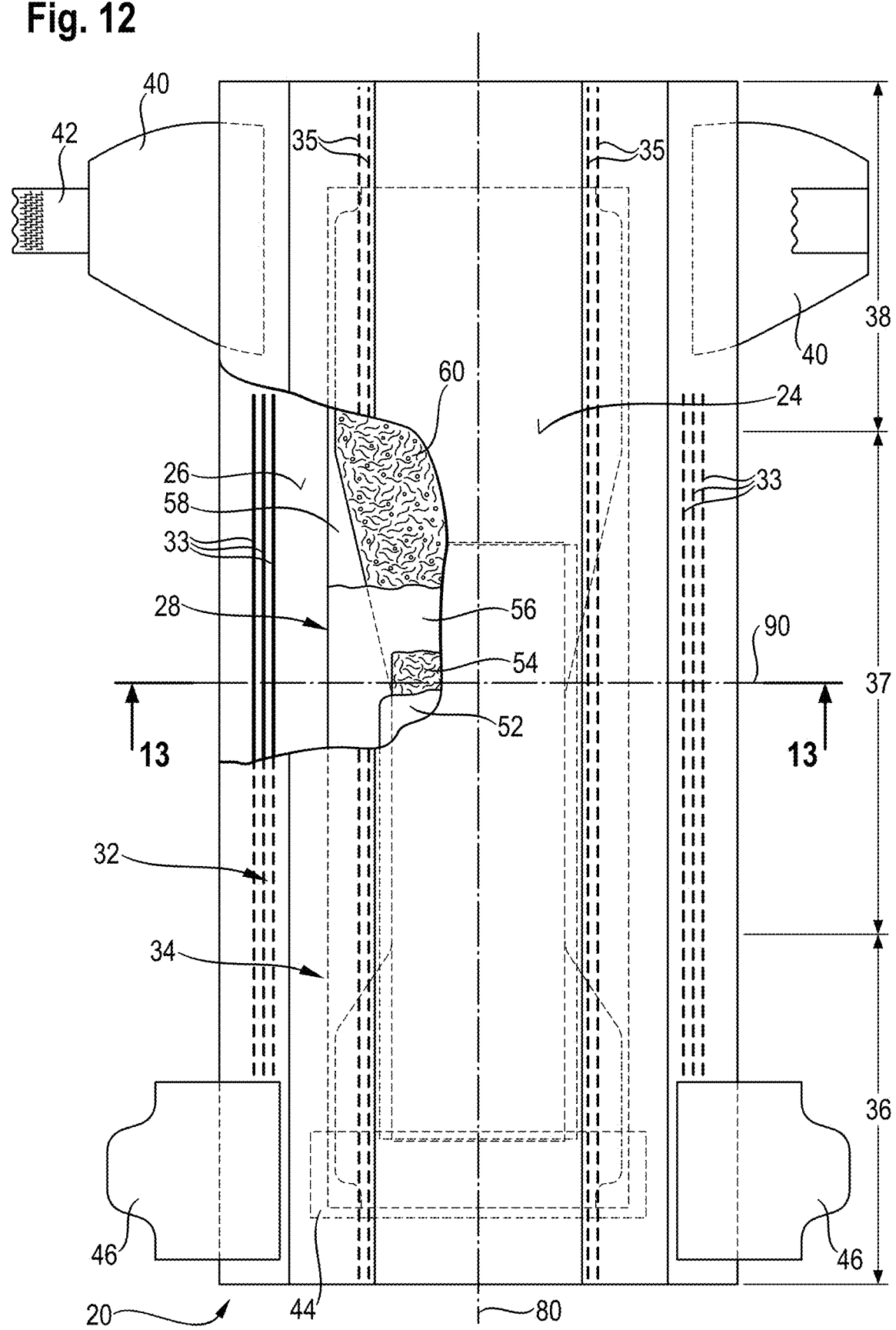
FIG. 12 is a top view of an exemplary absorbent article in the form of a diaper, which may comprise the topsheet of the present invention, with some layers partially removed.

In more details, FIG. 12 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbent articles.

Figure 13:
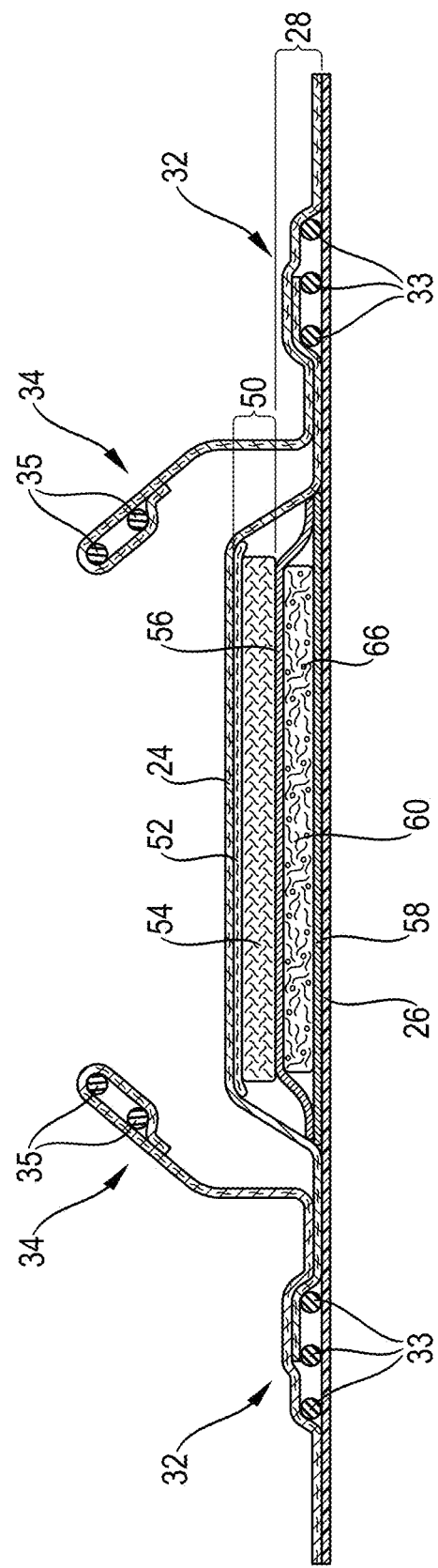
FIG. 13 is a transversal cross-section of the diaper of FIG. 12.

As shown in FIGS. 12 and 13, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as superabsorbent polymer particles 66 and/or cellulose fibers, as well as other absorbent and non-absorbent materials commonly used in absorbent articles (e.g. thermoplastic adhesives immobilizing the superabsorbent polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent core may comprise one or more substrate layer(s) (such as nonwoven webs or paper tissue), superabsorbent polymer particles disposed on the one or more substrate layers, and a thermoplastic composition typically disposed on the superabsorbent polymer particles. Typically the thermoplastic composition is a thermoplastic adhesive material. In one embodiment, the thermoplastic adhesive material forms a fibrous layer which is at least partially in contact with the superabsorbent polymer particles on the one or more substrate layers and partially in contact with the one or more substrate layers. Auxiliary adhesive might be deposited on the one or more substrate layers before application of the superabsorbent polymer particles for enhancing adhesion of the superabsorbent polymer particles and/or of the thermoplastic adhesive material to the respective substrate layer(s). The absorbent core may also include one or more cover layer(s) such that the superabsorbent polymer particles are comprised between the one or more substrate layer(s) and the one or more cover layer(s). The one or more substrate layer(s) and the cover layer(s) may comprise or consist of a nonwoven web. The absorbent core may further comprise odor control compounds.

The absorbent core may consist essentially of the one or more substrate layer(s), the superabsorbent polymer particles, the thermoplastic composition, optionally the auxiliary adhesive, optionally the cover layer(s), and optionally odor control compounds.

The absorbent core may also comprise a mixture of superabsorbent polymer particles and airfelt, which may be enwrapped within one or more substrate layers, such as nonwoven webs or paper tissue. Such absorbent cores may comprise from 30% to 95%, or from 50% to 95% of superabsorbent polymer particles by weight of the absorbent material and may comprise from 5% to 70%, or from 5% to 50% of airfelt by weight of the absorbent material (for these percentages, any enwrapping substrate layers are not considered as absorbent material). The absorbent core may also be free of airfelt and may comprise 100% of superabsorbent polymer particles by weight of the absorbent material.

The absorbent articles of the invention, especially diapers and pants, may comprise an acquisition layer 52, a distribution layer 54, or combination of both (all herein collectively referred to as acquisition-distribution system "ADS" 50).

A hydrophilic hot melt adhesive may be used to bond the topsheet to the acquisition layer and/or the distribution layer and/or the absorbent core. This may help to reduce the run-off.

The function of the ADS 50 is typically to quickly acquire the fluid and distribute it to the absorbent core in an efficient manner. The ADS may comprise one, two or more layers.

The ADS may be free of superabsorbent polymer. The prior art discloses many types of acquisition-distribution systems, see for example WO2000/59430, WO95/10996, U.S. Pat. No. 5,700,254, WO02/067809. However, the superabsorbent polymer particles may also be comprised by the ADS.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 g/m², in particular from 80 to 300 g/m².

The distribution layer 54 may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer 54 comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13 to 15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 12 and 13. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 12 and 13 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Figure 14:
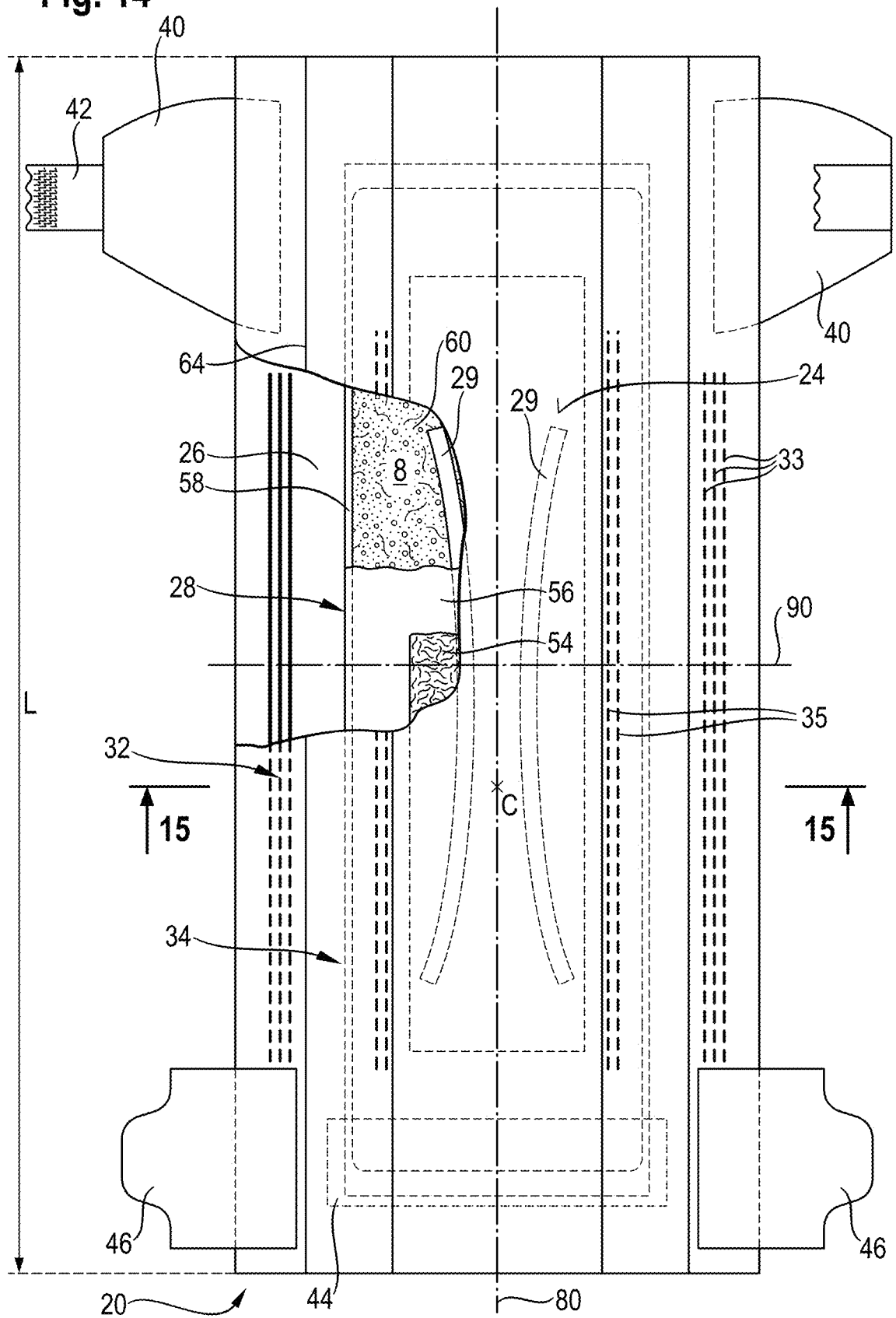
FIG. 14 is a top view of an exemplary absorbent article in the form of a diaper which may comprise the topsheet of the present invention, with area(s) substantially free of absorbent material.

Area(s) 29 Substantially Free of Absorbent Material and Channels 29':

As shown in FIG. 14, the absorbent core 28 may comprise one or more area(s) 29 which is/are substantially free of absorbent material. By "substantially free" it is meant that in each of these areas the basis weight of the absorbent material is less than 25%, in particular less than 20%, less than 10%, of the average basis weight of the absorbent material in the rest of the core. In particular there can be no absorbent material in these areas. Minimal amount such as involuntary contaminations with absorbent material that may occur during the making process are not considered as absorbent material. The areas 29 are advantageously surrounded by the absorbent material, when seen in the plane of the core, which means that the area(s) 29 does not extend to any of the edge of the deposition area 8 of the absorbent material.

Figure 15:
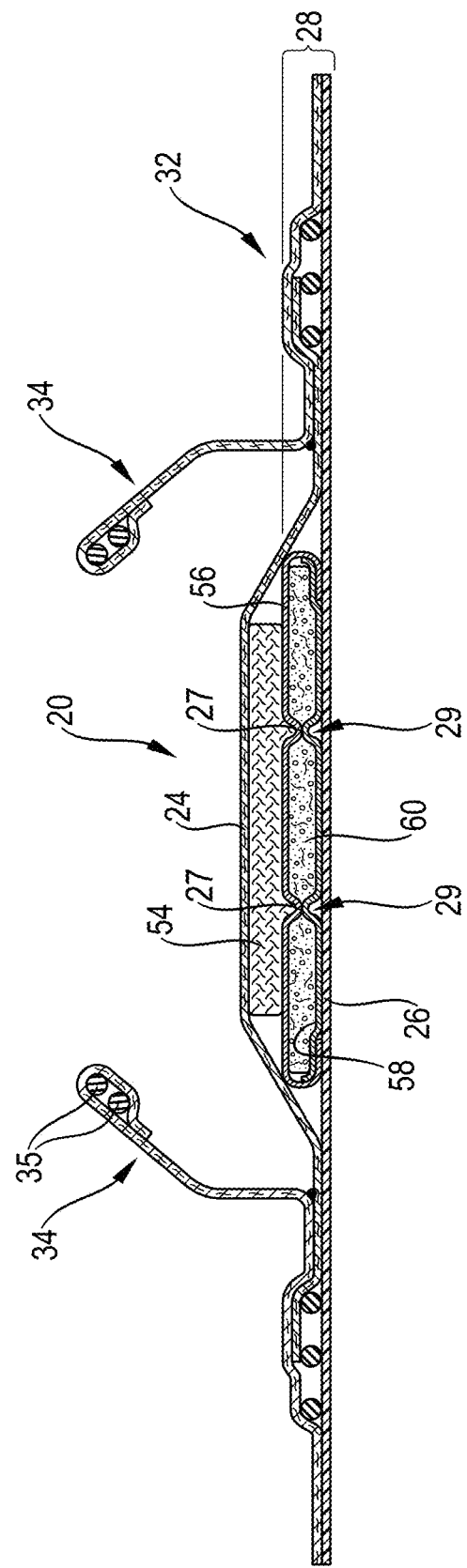
FIG. 15 is a transversal cross-section of the article of FIG. 14.
Figure 16:
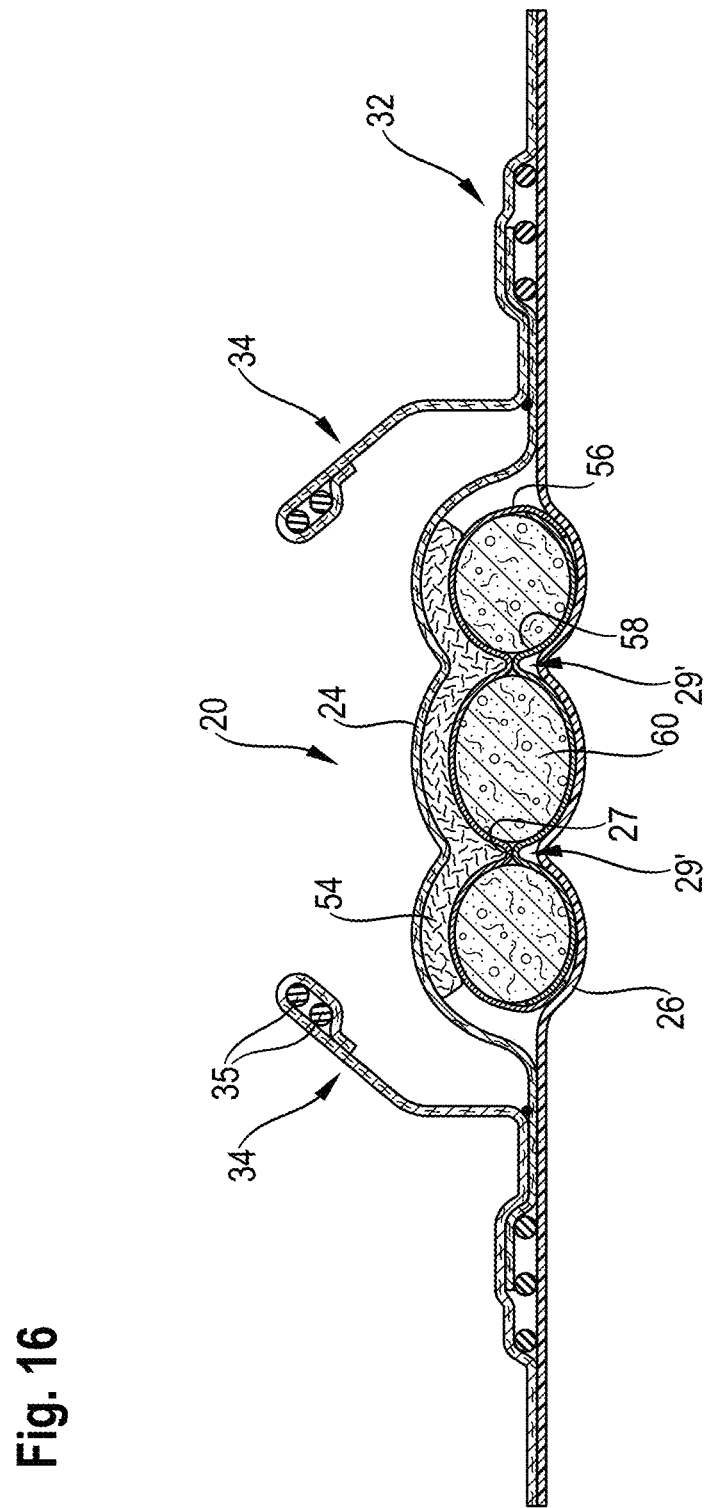
FIG. 16 is a transversal cross-section of the article taken at the same point as FIG. 15 where channels are formed in the core as a result of the diaper being loaded with fluid.

The upper core cover layer 56 is attached to the lower cover layer 58 by core wrap bond(s) 27 through these area(s) 29 substantially free of absorbent material. As shown in FIG. 15 and FIG. 16, when the absorbent material swells upon absorbing a liquid, the core wrap bond remains at least initially attached in the substantially material free area(s) 29. The absorbent material swells in the rest of the core when it absorbs a liquid, so that the core wrap forms one or more channel(s) 29' along the area(s) 29 substantially free of absorbent material comprising the core wrap bond 27. These channels 29' are three dimensional and can serve to distribute an insulting fluid along their length to a wider area of the core. This may provide a quicker fluid acquisition speed and a better utilization of the absorbent capacity of the core. The channels 29' can also provide a deformation of an overlying layer such as a fibrous layer 54 and provide corresponding ditches in the overlying layer. It is not excluded that the absorbent core may comprise other area(s) substantially free of absorbent material but without a core wrap bond, but these non-bonded areas will typically not form a channel when wet.

The upper core cover layer 56 and the lower cover layer 58 may be attached together continuously along the area(s) 29 substantially free of absorbent material, but the core wrap bond 27 may also be discontinuous (intermittent) such as series of point bonds. Typically, an adhesive can be used to attach the top side to the bottom of the core wrap, but it is possible to bond via other known attachment means, such as pressure bonding, ultrasonic bonding or heat bonding or combination thereof. The attachment of the top side and bottom side of the core wrap may be provided by one or more adhesive material, in particular one or more layers of auxiliary glue and/or one or more layers of fibrous adhesive material, if present in the core, as indicated below. These glues may therefore serve the dual function of immobilizing the absorbent material and attach the top side and the bottom side of the core together.

The following examples of the shape and size of the areas 29 substantially free of absorbent material are not limiting. In general, the core wrap bond 27 may have the same outline but be slightly smaller than the areas 29 due to the tolerance required in some manufacturing process. The substantially material free area(s) 29 may be present within the crotch region of the article, in particular at least at the same longitudinal level as the crotch point C, as represented in FIG. 14 by the two longitudinally extending areas substantially free of absorbent material 29. The absorbent core 28 may also comprise more than two substantially absorbent material free area(s), for example at least 3, or at least 4 or at least 5 or at least 6. The absorbent core may comprise one or more pairs of areas substantially free of absorbent material symmetrically arranged relative to the longitudinal axis 80. Shorter area(s) substantially free of absorbent material may also be present, for example in the back region or the front region of the core, as seen for example in the Figures of WO2012/170778.

The area(s) 29 substantially free of absorbent material may extend substantially longitudinally, which means typically that each area extends more in the longitudinal direction than in the transverse direction, and typically at least twice as much in the longitudinal direction than in the transverse direction (as measured after projection on the respective axis). The area(s) 29 substantially free of absorbent material may have a length projected on the longitudinal axis 80 of the core that is at least 10% of the length of the absorbent core, in particular from 20% to 80%. It may be advantageous that at least some or all of the area(s) 29 are not completely or substantially completely transversely oriented channels in the core.

The area(s) 29 substantially free of absorbent material may be completely oriented longitudinally and parallel to the longitudinal axis but also may be curved. In particular some or all these area(s), in particular these area(s) present in the crotch region, may be concave towards the longitudinal axis 80, as for example represented in FIG. 14 for the pair of channels 29'. The radius of curvature may typically be at least equal (and at least 1.5 or at least 2.0 times this average transverse dimension) to the average transverse dimension of the absorbent material deposition area 8; and also straight but under an angle of (e.g. from 5°) up to 30°, or for example up to 20°, or up to 10° with a line parallel to the longitudinal axis. The radius of curvature may be constant for a substantially absorbent material free area(s), or may vary along its length. This may also include area(s) substantially free of absorbent material with an angle therein, provided said angle between two parts of a channel is at least 120°, or at least 150°; and in any of these cases, provided the longitudinal extension of the area is more than the transverse extension. These area(s) may also be branched, for example a central substantially material free area superposed with the longitudinal axis in the crotch region which branches towards the back and/or towards the front of the article.

In some embodiments, there is no area(s) substantially free of absorbent material that coincides with the longitudinal axis 80 of the core. When present as one ore symmetrical pair(s) relative to the longitudinal axis, the area(s) substantially free of absorbent material may be spaced apart from one another over their whole longitudinal dimension. The smallest spacing distance may be for example at least 5 mm, or at least 10 mm, or at least 16 mm.

Furthermore, in order to reduce the risk of fluid leakages, the area(s) substantially free of absorbent material may advantageously not extend up to any of the edges of the absorbent material deposition area 8, and are therefore surrounded by and fully encompassed within the absorbent material deposition area 8 of the core. Typically, the smallest distance between an area(s) substantially free of absorbent material and the closest edge of the absorbent material deposition area is at least 5 mm.

The area(s) substantially free of absorbent material may have a width Wc along at least part of its length which is at least 2 mm, or at least 3 mm or at least 4 mm, up to for example 20 mm, or 16 mm or 12 mm. The width Wc of the area(s) substantially free of absorbent material may be constant through substantially its whole length or may vary along its length.

The channels 29' in the absorbent core start forming when the absorbent material absorbs a liquid such as urine and starts swelling. As the core absorbs more liquid, the depressions within the absorbent core formed by channels will become deeper and more apparent to the eye and the touch. It is possible to create a sufficiently strong core wrap bond combined with a relatively low amount of superabsorbent polymer particles so that the channels remain permanent until complete saturation of the absorbent material. On the other hand, the core wrap bonds may in some cases also restrict the swelling of the absorbent material when the core is substantially loaded.

Initially, the core wrap bond(s) may be designed to be closed and to increase the pressure in the areas adjacent to the core wrap bond(s). At some point, the core wrap bond 27 may also be designed to open in a controlled manner when exposed to a large amount of fluid.

Test Methods

Figure 17:
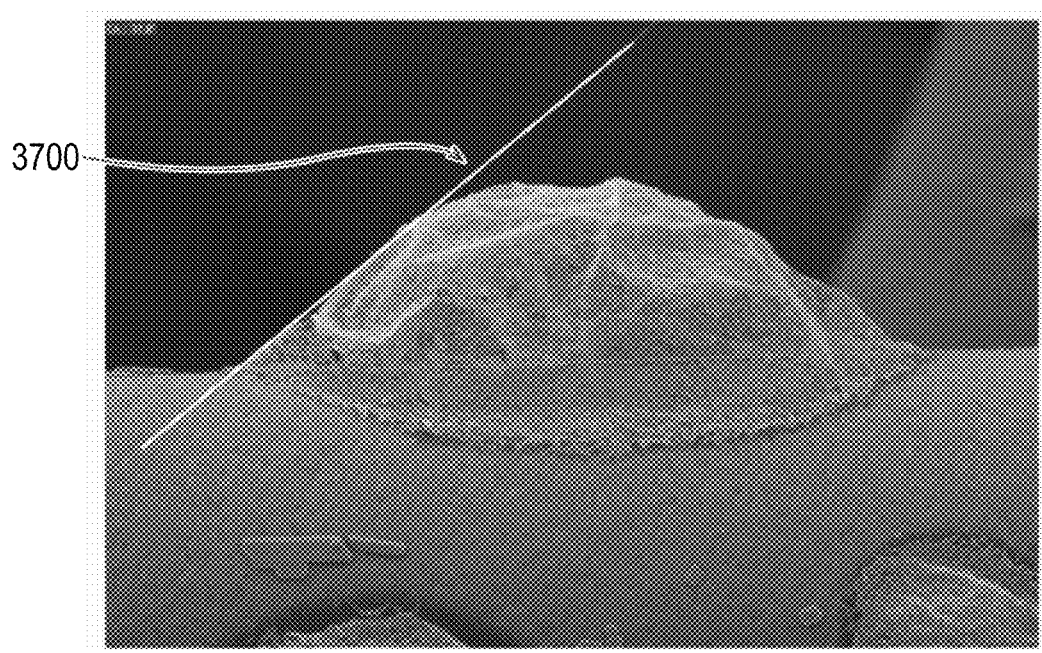
FIG. 17 is a photomicrograph depicting exemplary water droplet on fibers for the Contact Angle Test Method disclosed herein.

Contact Angle Test Method:

A rectangular specimen measuring 1 cm×2 cm is cut from the topsheet of a disposable absorbent product taking care not to touch the surface of the specimen or to disturb the structure of the material. The specimen has a length of (2 cm) aligned with a longitudinal centerline of the article. The specimen is handled gently by the edges using forceps and is mounted flat with the skin-facing side up on an SEM specimen holder using double-sided tape. The specimen is sprayed with a fine mist of water droplets generated using a small hobby air-brush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Cryo-SEM prep chamber at −150° C., coated with Au/Pd, and transferred into Cryo-SEM chamber at −150° C. A Hitachi S-4700 Cry-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the image taken as is shown via lines 3700 in FIG. 17.

Such method is performed on the land region of the first surface of the first layer to measure the First Surface Land Area Contact Angle. Ten separate droplets, located on the land area in the middle between two neighboring apertures, are imaged from which twenty contact angle measurements are performed (one on each side of each imaged droplet), and the arithmetic average of these twenty contact angle measurements is calculated and reported as the First Surface Land Area Contact Angle.

Such method is also performed on the apertures to measure the Apertures Contact Angle. Ten separate droplets, located near the top of three separate apertures, and ten droplets, located near the bottom of the same three separate apertures, are imaged from which forty contact angle measurements are performed (one on each side of each imaged droplet), and the arithmetic average of these forty contact angle measurements is calculated and reported as the Apertures Contact Angle.

Percent Effective Area, Aperture Dimension and Inter-Aperture Distance Measurement Test Method:

Effective aperture dimensions, percent effective area and inter-aperture distance measurements are obtained from aperture specimen images acquired using a flatbed scanner. The scanner is capable of scanning in reflectance mode at a resolution of 6400 dpi and 8 bit grayscale (a suitable scanner is an Epson Perfection V750 Pro from Epson America Inc., Long Beach Calif., or equivalent). The scanner is interfaced with a computer running an image analysis program (a suitable program is ImageJ v. 1.47, National Institute of Health, USA, or equivalent). The specimen images are distance calibrated against an acquired image of a ruler certified by NIST. The aperture specimen is backed with a black glass tile (P/N 11-0050-30, available from HunterLab, Reston, Va., or equivalent) prior to acquiring the image. The resulting grayscale image is then converted to a binary image via a threshold gray-level value, enabling the separation of open aperture regions from specimen material regions, and these regions analyzed using the image analysis program. All testing is performed in a conditioned room maintained at about 23±2° C. and about 50±2% relative humidity.

Sample Preparation:

To obtain a specimen, the absorbent article is taped to a rigid flat surface in a planar configuration. Any leg elastics present may be cut to facilitate laying the article flat. The outer boundary of the region lying above the absorbent core of the article is identified and marked on the apertured layer. The specimen of apertured layer is removed from the underlying layers of the article by cutting around the outer perimeter of the article with a razor blade. The apertured layer specimen is carefully removed such that its longitudinal and lateral extension is maintained to avoid distortion of the apertures. A cryogenic spray (such as Cyto-Freeze, Control Company, Houston Tex., or equivalent) can be used to remove the specimen from the underlying layers if necessary. Five replicate specimens obtained from five substantially similar articles are prepared for analysis. An apertured substrate raw material is prepared for testing by extending or activating it under the same process conditions, and to the same extent, as it would be for use on the absorbent article. The samples are conditioned at about 23° C.±2 C° and about 50%±2% relative humidity for 2 hours prior to testing.

Image Acquisition:

The ruler is placed on the scanner bed such that it is oriented parallel to the sides of the scanner glass. An image of the ruler (the calibration image) is acquired in reflectance mode at a resolution of 6400 dpi (approximately 252 pixels per mm) and in 8-bit grayscale. The calibration image is saved as an uncompressed TIFF format file. After obtaining the calibration image, the ruler is removed from the scanner glass and all specimens are scanned under the same scanning conditions. An apertured specimen is placed onto the center of the scanner bed, lying flat, with the outward facing surface of the specimen facing the scanner's glass surface. The corners and edges of the specimen are secured such that its original longitudinal and lateral extension, as on the article prior to removal, is restored. The specimen is oriented such that the machine direction (MD) and cross direction (CD) of the apertured specimen layer are aligned parallel with and perpendicular to the sides of the scanner's glass surface and that the resulting specimen image has the MD vertically running from top to bottom. The black glass tile is placed on top of the specimen, the scanner lid is closed, and a scanned image of the entire specimen is acquired. The specimen image is save as an uncompressed TIFF format file. The remaining four replicate specimens are scanned and saved in like fashion. Prior to analysis, all specimen images are cropped to the largest rectangular field of view contained within the apertured region which had been located above the absorbent core of the article.

Percent Effective Aperture Area Calculation:

The calibration image file is opened in the image analysis program and a linear distance calibration is performed using the imaged ruler. This distance calibration scale is applied to all subsequent specimen images prior to analysis. A specimen image is in the image analysis program and the distance scale is set using the distance calibration. The 8-bit grayscale image is then converted to a binary image (with "zero" or "black" corresponding to the aperture regions) in the following way: If the histogram of gray level (GL) values (ranging from 0 to 255, one bin with propensity Pi per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined.

Each of the discrete aperture regions is analyzed using the image analysis program. All individual aperture areas are measured and recorded to the nearest 0.01 mm$^2$, including partial apertures along the edges of the image. Any apertures with an area less than 0.3 mm$^2$ are defined as "non-effective" and discarded. The remaining apertures, so-called "effective" aperture areas that include whole and partial apertures, are summed. This sum is then divided by the total area included in the image. This value is multiplied by 100% and reported as the effective area to the nearest 0.01%.

The remaining four specimen images are analyzed similarly. The average percent effective area values to the nearest 0.01% for the five replicate specimens are calculated and reported.

Effective Aperture Dimension Measurements:

The calibration image (containing the ruler) file is opened in the image analysis program. The resolution of the original image is resized from 6400 dpi to 640 dpi (approximately 25.2 pixels per mm) using a bicubic interpolation. A linear distance calibration is performed using the imaged ruler. This distance calibration scale is applied to all subsequent specimen images prior to analysis. One specimen image is selected and opened in the image analysis program. The resolution of the original image is resized from 6400 dpi to 640 dpi (approximately 25.2 pixels per mm) using a bicubic interpolation, and a distance scale is set according to the linear distance calibration established using the calibration image. The 8-bit grayscale image is then converted to a binary image (with "zero" or "black" corresponding to the aperture regions) in the following way: If the histogram of gray level (GL) values (ranging from 0 to 255, one bin with propensity Pi per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t$ $P_{t+1}$. This procedure identifies the gray level (GL) value for the minimum population located between the dark pixel peak of the aperture holes and the lighter pixel peak of the specimen material. If the histogram contains either zero or one local maximum, the method cannot proceed further, and no output parameters are defined. Two morphological operations are then performed on the binary image. First, a closing (a dilation operation, which converts any white background pixel that is touching a black aperture region pixel into a black aperture region pixel thereby adding a layer of pixels around the periphery of the aperture region, followed by an erosion operation, which removes any black aperture region pixel that is touching a white background pixel thereby removing a layer of pixels around the periphery of the aperture region, iterations=1, pixel count=1) is performed, which removes stray fibers within an aperture hole. Second, an opening (an erosion operation followed by a dilation operation, iterations=1, pixel count=1) is performed, which removes isolated black pixels. The edges of the image are padded during the erosion step to ensure that black boundary pixels are maintained during the operation. Lastly, any remaining voids enclosed within the black aperture regions are filled.

Each of the discrete aperture regions is analyzed using the image analysis software. Any partial apertures along the edges of the image are excluded so that only whole apertures are analyzed. All of the individual aperture areas, perimeters, feret diameters (length of the apertures) along with its corresponding angle of orientation in degrees from 0 to 180, and minimum feret diameters (width of the apertures) are measured and recorded. Individual aperture areas are recorded to the nearest 0.01 $mm^2$, aperture perimeters and feret diameters (length and width), to the nearest 0.01 mm, and aperture angles to the nearest 0.01 degree. Any apertures with an area less than 0.3 $mm^2$ are discarded as "non-effective". The number of remaining "effective" apertures is recorded and divided by the area of the image. This quotient is recorded as the Aperture Density value to the nearest 0.1 apertures per $cm^2$. The angle of orientation for an aperture aligned with the MD (vertical in the image) is defined as 90 degrees. Apertures with a positive slope, increasing from left to right, have an angle between zero and 90 degrees. Apertures with a negative slope, decreasing from left to right, have an angle between 90 and 180 degrees. The angles of individual apertures are used to calculate an Absolute Aperture Angle by subtracting 90 degrees from the original angle of orientation and taking its absolute value. In addition to these measurements, the Aspect Ratio, defined for each aperture as the quotient of its length divided by its width, is recorded. This analysis is repeated for each of the remaining images of the four replicate specimens. The statistical mean and standard deviation for each of the effective aperture dimensions (area, perimeter, length, width, and angle), the Absolute Aperture Angle and the Aspect Ratio measurements are calculated and using all of the aperture values recorded from all specimens and reported. The percent relative standard deviation (RSD) for each of the effective aperture dimensions, the Absolute Aperture Angle and the Aspect Ratio measurements is calculated and reported by dividing the standard deviation by the mean and multiplying by 100%.

Inter-Aperture Distance Measurements:

The mean, standard deviation, median, and maximum distance between the apertures are measured by further analyzing the binary images for each specimen that were analyzed for the aperture dimension measurements. For each image, a Voronoi operation is performed on a resized, spatially calibrated, binary image (described above). The Voronoi operation generates an image in which regions or "cells" bounded by lines of pixels having equal distance to the borders of the two nearest pattern apertures in which the pixel values of these boundary lines are outputs from a Euclidian distance map (EDM) of the binary image and in which all other pixel values are zero. (An EDM is a transformed image in which each inter-aperture pixel in the binary image is replaced with a value equal to that pixel's distance from the nearest pattern aperture.) Statistical analysis of the nonzero distance values (that is, the Euclidean distance values along the boundary lines) present in the Voronoi-transformed image is performed. The resulting mean, standard deviation, median and maximum inter-aperture distances for the image are calculated and then multiplied by a factor of two to reflect full distance between aperture features. These statistical metrics are reported to the nearest 0.01 mm. This procedure is repeated for all specimen images. The percent relative standard deviation (RSD) for the inter-aperture distance by dividing the standard deviation by the mean and multiplying by 100%.

Post-Conditioning Contact Angle Test Method:

A topsheet specimen is removed from an absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of a 10±1 cm×10±1 cm area. If the topsheet is of insufficient size to permit a 10±1 cm×10±1 cm area to be excised from the intersection of the longitudinal and lateral centerlines, the largest square of topsheet that can be extracted is excised and used as the topsheet specimen henceforth. The specimen is carefully removed such that its longitudinal and lateral extension are maintained. A cryogenic spray (such as Cyto- Freeze, Control Company, Houston Tex.) can be used to remove the topsheet specimen from the underling layers, if necessary.

A solution (the "conditioning solution") is prepared with 0.9% (w/w) NaCl and 0.3% (w/w) Na-cholate by using distilled water, NaCl with purity higher than 99% and NA-cholate with purity higher than 96%. The conditioning solution is heated to 40±2° C. and is held as this temperature for the entirety of this sample preparation. 100 (+/−10) ml of the temperature-maintained conditioning solution is filled into a glass container with a diameter of 150 to 180 mm. The test specimen is put into the glass container with the conditioning solution by keeping the specimen beneath the surface of the solution, and the glass container is placed into a climate chamber at 40 (+/−2) ° C. for 30±2 minutes.

The test specimen is then taken out of the solution by using clean metal tweezers and placed on blotting paper (larger than the test specimen). Once the blotting paper is partly wetted, new blotting paper is used. This is repeated until no further wetness is transferred to the blotting paper. The specimen is then transferred to a dry clean glass container with a diameter of 150 to 180 mm, and the glass container is placed into a climate chamber at 40 (+/−2) ° C. for 30 (+/−2) minutes. The specimen is then let cool down to room temperature. A rectangular specimen, measuring 1 cm×2 cm, is cut from the conditioned test specimen, according to the Contact Angle Method. The First Surface Land Area contact angle of the specimen after conditioning, measured according to the Contact Angle Method, is reported as the First Surface Land Area Post-Conditioning Contact Angle.

Run-Off Test Method:

Run-off is measured according to basic method for testing hydrophilic nonwovens in WSP 80.9 (05), standard test method for nonwoven run-off. The inclination angle is set to be 25°+/−1°. A total mass of test liquid of 25±0.5 g is used.

The topsheet sample is removed from the absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of the 100 mm×280 mm area. The specimen is carefully removed such that its longitudinal and lateral extension are maintained. A cryogenic spray (such as Cyto-Freeze, Control Company, Houston Tex.) can be used to remove the topsheet specimen from the underling layers, if necessary. The topsheet layer with 100 mm width is centered over the two 140 mm wide layers of reference filter paper.

If the dimensions of the absorbent article do not allow to excise an area of 100 mm×280 mm, then the largest possible rectangular topsheet area will be excised from the absorbent article with the procedure above. Multiple specimens will be removed from multiple absorbent articles and will be connected to each other with a 5 mm wide overlap on each neighboring side between two separate pieces. A double tape adhesive will be placed in the 5 mm wide overlap area, between the two layers being stitched together. This procedure will allow to create a 100 mm×280 mm area to be used according to basic method for testing hydrophilic nonwovens in WSP 80.9 procedure. For the testing, the tube, supplying the test liquid, will be placed between any overlap areas, in machine direction or cross direction.

Capillary Drainage Test Method:

The Capillary Drainage Test Method is used to determine the average amount of fluid (g/g) retained by three specimens at a differential pressure of 300 mm H$_2$O. This method makes use of stepped, controlled differential pressure and measurement of associated fluid movement into and out of a porous specimen. The fluid retained (g/g) by each specimen during its first drainage cycle at 300 mm H$_2$O of differential pressure is measured and the average value obtained from three like specimens is reported as the parameter CDP300.

Method Principle:

For uniform cylindrical pores, the radius of a pore is related to the differential pressure required to fill or empty the pore by the equation $$\text{Differential pressure} = (2\gamma \cos \Theta)/r,$$

where $\gamma$=liquid surface tension, $\Theta$=contact angle, and $r$=pore radius.

Pores contained in natural and manufactured porous materials are often thought of in terms such as voids, holes or conduits, and these pores are generally not perfectly cylindrical nor all uniform. One can nonetheless use the above equation to relate differential pressure to an effective pore radius, and by monitoring liquid movement into or out of the material as a function of differential pressure characterize the effective pore radius distribution in a porous material. (Because nonuniform pores are approximated as uniform by the use of an effective pore radius, this general methodology may not produce results precisely in agreement with measurements of void dimensions obtained by other methods such as microscopy).

The Capillary Drainage Test Method uses the above principle and is reduced to practice using the apparatus and approach described in "Liquid Porosimetry: New Methodology and Applications" by B. Miller and I. Tyomkin published in The Journal of Colloid and Interface Science (1994), volume 162, pages 163-170, incorporated herein by reference. This method relies on measuring the increment of liquid volume that enters or leaves a porous material as the differential air pressure is changed between ambient ("lab") air pressure and a slightly elevated air pressure (positive differential pressure) surrounding the specimen in a sample test chamber. The specimen is introduced to the sample chamber dry, and the sample chamber is controlled at a positive differential pressure (relative to the lab) sufficient to prevent fluid uptake into the specimen after the fluid bridge is opened. After opening the fluid bridge, the differential air pressure is decreased in steps to 0, and in this process subpopulations of pores acquire liquid according to their effective pore radius. After reaching a minimal differential pressure at which the mass of fluid within the specimen is at a maximum, differential pressure is increased stepwise again toward the starting pressure, and the liquid is drained from the specimen. It is during this latter draining sequence (from minimal differential pressure, or largest corresponding effective pore radius, to the largest differential pressure, or smallest corresponding effective pore radius), that the fluid retention by the sample (g/g) at each differential pressure is determined in this method. After correcting for any fluid movement for each particular pressure step measured on the chamber while empty, the fluid retention by the sample (g/g) for each pressure step is determined via dividing the equilibrium quantity of retained liquid (g) associated with this particular step by the dry weight of the sample (g).

Sample Conditioning and Specimen Preparation:

A topsheet specimen is removed from an absorbent article, centered at the intersection of the longitudinal and lateral centerlines of the absorbent article: for the purpose of removing the topsheet from the absorbent article, a razor blade is used to excise the topsheet from the underling layers of the absorbent article around the outer perimeter of a 7±1 cm×7±1 cm area. (If the topsheet is of insufficient size to permit a 7±1 cm×7±1 cm area to be excised from the intersection of the longitudinal and lateral centerlines, the largest square of topsheet that can be extracted is excised and used as the topsheet specimen henceforth). The specimen is carefully removed such that its longitudinal and lateral extension are maintained. If the topsheet is made of two layers, the first layer, comprising at least 15% by weight of natural fibers by total weight of the first layer, is separated and used for the Capillary Drainage Test Method measurement. A cryogenic spray (such as Cyto-Freeze, Control Company, Houston Tex.) can be used to remove the topsheet specimen from the underling layers, if necessary. A circular sample with a diameter of 50 mm is obtained from the topsheet specimen removed from the absorbent article.

The Capillary Drainage Test Method is conducted on samples that have been conditioned in a room at a temperature of 23° C.±2.0° C. and a relative humidity of 50%±5%, all tests are conducted under the same environmental conditions and in such conditioned room. Any damaged product or samples that have defects such as wrinkles, tears, holes, and similar are not tested. Samples conditioned as described herein are considered dry samples for purposes of this invention. Three specimens are measured for any given material being tested, and the results from those three replicates are averaged to give the final reported value. Each of the three replicate specimens has a diameter of 50 mm.

Apparatus:

Apparatus suitable for this method is described in: "Liquid Porosimetry: New Methodology and Applications" by B. Miller and I. Tyomkin published in The Journal of Colloid and Interface Science (1994), volume 162, pages 163-170. Further, any pressure control scheme capable of controlling the sample chamber pressure between 0 mm $H_2O$ and 1200 mm $H_2O$ differential pressure may be used in place of the pressure-control subsystem described in this reference. One example of suitable overall instrumentation and software is the TRI/Autoporosimeter (Textile Research Institute (TRI)/Princeton Inc. of Princeton, N.J., U.S.A.). The TRI/Autoporosimeter is an automated computer-controlled instrument for measuring pore volume distributions in porous materials (e.g., the volumes of different size pores within the range from 1 to 1000 μm effective pore radii). Computer programs such as Automated Instrument Software Releases 2000.1 or 2003.1/2005.1 or 2006.2; or Data Treatment Software Release 2000.1 (available from TRI Princeton Inc.), and spreadsheet programs may be used to capture and analyze the measured data.

Method Procedure:

The wetting liquid used is a degassed 0.9% NaCl solution. Liquid density is 1.01 $g/cm^3$, surface tension γ to be 72.3±1 mN/m, and the contact angle cos Θ=0.37. A 90-mm diameter mixed-cellulose-ester filter membrane with a characteristic pore size of 1.2 μm (such Millipore Corporation of Bedford, Mass., Catalogue #RAWP09025) is affixed to the porous frit (Monel plates with diameter of 90 mm, 6.4 mm thickness from Mott Corp., Farmington, Conn., or equivalent) of the sample chamber.

Someone skilled in the art knows that it is critical to degas the test fluid as well as the frit/membrane/tubing system such that the system is free from air bubbles.

A metal weight weighing 414 g is placed on top of the sample to exert a constant confining pressure of 2.068 kPa during measurement.

The sequence of differential pressures that are run in the test, in mm $H_2O$, is as follows: 800, 400, 380, 360, 340, 320, 300, 280, 265, 250, 235, 220, 205, 190, 175, 160, 145, 130, 115, 100, 90, 80, 70, 60, 55, 50, 45, 40, 35, 30, 25, 20, 15, 10, 5, 0, 5, 10, 15, 20, 25, 30, 35, 40, 45, 50, 55, 60, 70, 80, 90, 100, 115, 130, 145, 160, 175, 190, 205, 220, 235, 250, 265, 280, 300, 320, 340, 360, 380, 400, 800.

The criterion for moving from one pressure step to the next is that fluid uptake/drainage from the specimen is measured to be less than 10 mg/min for 15 s.

A separate "blank" measurement is performed by following this method procedure on an empty sample chamber with no specimen or weight present on the membrane/frit assembly. Any fluid movement observed is recorded (g) at each of the pressure steps. Fluid retention data for a specimen are corrected for any fluid movement associated with the empty sample chamber by subtracting fluid retention values of this "blank" measurement from corresponding values in the measurement of the specimen.

Determination of Capillary Drainage Parameter:

As described above, for each of the three specimens, the capillary fluid retained (g) by each specimen during its first drainage cycle at 300 mm $H_2O$ of differential pressure is corrected for any effect of the empty chamber and then divided by the dry mass of the specimen to arrive at capillary fluid drained normalized by dry sample mass in units of g/g. The arithmetic mean of three values for the normalized capillary fluid drained from the three samples is reported as the parameter CDP300 (drainage uptake at 30 cm-water) in g/g.

EXAMPLES

The following are non-limiting examples of the topsheet of the present invention and of comparative examples. The examples are given solely for the purpose of illustration and are not to be construed as limitations of the present invention, as many variations thereof are possible without departing from the spirit and scope of the invention, which would be recognized by one of ordinary skill in the art.

Preparation of the Samples:

All the following examples are topsheets comprising two layers, a first layer and a second layer, bonded with a hydrophobic hot melt adhesive, applied to the second layer. The first layer is a three-dimensional layer while the second layer is flat. The apertures of the first layer are aligned with the apertures of the second layer. The topsheets of each example are formed according to the processes described above (see FIGS. 7-11). For every example using hydrophobic surfactant, the hydrophobic surfactant is the same.

Example 1 is a topsheet comprising a first layer being a 100% cotton spunlace nonwoven and a second layer being a SMS nonwoven (Spunbond-Meltblown-Spunbond). The first layer is treated with a hydrophobic surfactant via dipping process. The second layer is hydrophilic. The basis weight of the first layer is 30 gsm. The basis weight of the second layer is 8 gsm. The basis weight of the hot melt adhesive applied to the second layer is 1 gsm.

Example 2 is a topsheet comprising a first layer being a 100% cotton spunlace nonwoven and a second layer being a SMS nonwoven (Spunbond-Meltblown-Spunbond). The first layer is treated with a hydrophobic surfactant via dipping process. The second layer is hydrophilic. The basis weight of the first layer is 30 gsm. The basis weight of the second layer is 8 gsm. The basis weight of the hot melt adhesive applied to the second layer is 2.5 gsm. The second layer is treated with 2.7 gsm of a hydrophilic surfactant via spraying and then the second layer is dried. It makes the apertures more hydrophilic.

Example 3 is a topsheet comprising a first layer being a 100% cotton spunlace nonwoven and a second layer being a resin bonded carded nonwoven with 6 and 9 denier PET fibers. The first layer is treated with a hydrophobic surfactant via dipping process. The second layer is hydrophilic. The basis weight of the first layer is 30 gsm. The basis weight of the second layer is 33 gsm. The basis weight of the hot melt adhesive applied to the second layer is 2.5 gsm. The second layer is treated with 5.4 gsm of a hydrophilic surfactant via spraying and then the second layer is dried. It makes the apertures more hydrophilic.

Example 4 is a topsheet comprising a first layer being a 100% cotton spunlace nonwoven and a second layer being a SMS nonwoven (Spunbond-Meltblown-Spunbond). The basis weight of the first layer is 30 gsm. The basis weight of the second layer is 8 gsm. The basis weight of the hot melt adhesive applied to the second layer is 1 gsm. The first layer is hydrophilic. The second layer is hydrophilic.

Example 5 is a topsheet comprising a first layer being a 100% cotton spunlace nonwoven and a second layer being a carded air-through nonwoven with 2 denier PE/PET bico fibers. The first layer is treated with a hydrophobic surfactant via dipping process. The second layer is hydrophilic. The basis weight of the first layer is 30 gsm. The basis weight of the second layer is 50 gsm. The basis weight of the hot melt adhesive applied to the second layer is 2 gsm. A hydrophilic surfactant is deposited to the apertures via pin process.

Examples 1 and 4 are comparative examples. Examples 2, 3 and 5 are topsheets according to the invention.

Results:

The contact angle on the land areas or on the apertures, the run-off, the CDP300, the apertures width, length, perimeter and area are measured according to the corresponding test methods disclosed herein.

|  | Example 1 | Example 2 | Example 3 | Example 4 | Example 5 |
| --- | --- | --- | --- | --- | --- |
| Land areas (first surface) Contact Angle (in°) | 101 | 89 | 81 | — | — |
| Apertures Contact Angle (in°) | 94 | 60 | 57 | — | — |
| Land areas Post-Conditioning Contact Angle (in°) | 73 | — | 64 | — | — |
| Percent Effective Aperture Area (in %) | 5.04 | 7.19 | — | — | — |
| Aperture Area (in mm$^2$) | 0.76 | 0.73 | 0.44 | — | — |
| Aperture Perimeter (in mm) | 3.5 | 3.52 | 3.36 | — | — |
| Aperture Length (in mm) | 1.26 | 1.37 | 1.03 | — | — |
| Aperture Width (in mm) | 0.85 | 0.74 | 0.75 | — | — |
| Aperture Density (in number of apertures/cm$^2$) | 7.1 | 11 | — | — | — |
| Aperture Aspect Ratio | 1.49 | 1.88 | 1.4 | — | — |
| Run-off (in %) | 71 | — | 3 | 4 | 0.2 |
| CDP300-drainage uptake at 30 cm-water (in g/g) | 0.35 | 1.72 | 1.83 | 3.20 | 1.79 |

The contact angle on the land areas of the first layer of the topsheet of examples 1, 2 and 3 between the majority of the apertures is more than 70°, according to the Contact Angle Test Method. Therefore, the first layer of the examples 1, 2 and 3 is hydrophobic.

The contact angle on the majority of the apertures of the topsheet of example 1 is more than 70°, according to the Contact Angle Test Method. The majority of the apertures of the topsheet of example 1 is hydrophobic.

The contact angle on the majority of the apertures of the topsheet of examples 2 and 3 is less than 70°, according to the Contact Angle Test Method. The majority of the apertures of the topsheet of examples 2 and 3 are hydrophilic.

Comparative example 1 shows a high run-off compared to example 3 of the invention. Therefore, there is a high risk of leakage when the topsheet of example 1 is used in an absorbent article.

The topsheet of example 3 of the invention has a run-off of less than 40%, according to the Run-off Test Method. Therefore, the topsheet of example 3 of the invention is adequately dry and absorbs body fluids with low run-off. It results in reduced risk of body fluids leakage when the topsheet is used in an absorbent article.

The topsheet of example 3 of the invention allows a better absorption of body fluids. The topsheet of example 3 of the invention reduces the contact of the liquid bodily exudates with the skin of the wearer. Therefore, the topsheet of example 3 of the invention is sufficiently dry when in contact with the skin of the wearer.

Moreover, the topsheet of example 3 and of example 2 of the invention have a contact angle on the land areas of the first layer of the topsheet of more than 50°, according to the Post-conditioning Contact Angle Test Method. It enables to have topsheets with no wetness/rewet issues after prolonged wear time.

Comparative example 4 has a low run-off but a drainage uptake of more than 2 g/g at 30 at 30 cm-water, according to the Capillary Drainage Test Method. Thus, the topsheet of example 4, when used in an absorbent article, does not allow a rapid passage of the body fluids through its thickness toward the absorbent article's inner region.

The topsheet of example 5 of the invention has a run-off of less than 40%, according to the Run-off Test Method and a drainage uptake of less than 2 g/g at 30 cm-water, according to the Capillary Drainage Test Method. Therefore, the topsheet of example 5 of the invention is adequately dry and absorbs body fluids with low run-off.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topsheet for use in an absorbent article having at least a first layer, wherein the first layer comprises at least 15% by weight of natural fibers by total weight of the first layer;
wherein the first layer has a plurality of apertures;
wherein the first layer comprises land areas between at least a plurality of the apertures;
wherein a contact angle on the land areas of the first layer between the plurality of the apertures is more than 70°, according to a Contact Angle Test Method described herein;
wherein a majority of the plurality of the apertures comprise a hydrophilic material; and
wherein the topsheet has a run-off of less than 40%, according to a Run-off Test Method described herein;
wherein the first layer comprises a plurality of protrusions, wherein the plurality of protrusions impart a three-dimensional shape to the first layer, and wherein the plurality of the apertures are located between the plurality of the protrusions;
wherein the topsheet comprises a second layer in a face to face relationship with the first layer, and wherein the first layer and the second layer are in contact with each other between the plurality of the protrusions;
wherein the second layer has a plurality of apertures at least partially aligned with the plurality of apertures of the first layer;
wherein the first layer at least partially penetrates the second layer of the topsheet at the plurality of the apertures;
wherein the second layer comprises land areas between the plurality of the apertures; and
wherein the second layer comprises synthetic fibers, natural fibers or combinations thereof.

2. The topsheet of claim 1, wherein the topsheet has a run-off of less than 20%, according to the Run-off Test Method.

3. The topsheet of claim 1, wherein the plurality of apertures are uniformly distributed along a first surface of the first layer.

4. The topsheet of claim 1, wherein the first layer comprises at least 30% by weight of natural fibers by total weight of the first layer.

5. The topsheet of claim 1, wherein the contact angle on the land areas of the first layer after a conditioning process is more than 50°, according to a Post-conditioning Contact Angle Test Method described herein.

6. The topsheet of claim 1, wherein a width of the plurality of the apertures is at least 0.8 mm, according to an Aperture Dimension Test Method described herein.

7. The topsheet of claim 1, wherein a contact angle on the majority of the plurality of the apertures is less than or equal to 70°, according to the Contact Angle Test Method.

8. The topsheet of claim 7, wherein the plurality of the apertures of the first layer of the topsheet have at least 4% of hydrophilic open area.

9. The topsheet of claim 7, wherein the topsheet has a drainage uptake of less than 2 g/g at 30 cm-water, according to a Capillary Drainage Test Method described herein.

10. The topsheet of claim 9, wherein a width of the plurality of the apertures is less than 1.5 mm, according to an Aperture Dimension Test Method described herein.

11. The topsheet of claim 1, wherein the second layer is substantially flat, wherein a contact angle on the land areas of the second layer between the plurality of the apertures is less than or equal to 70° according to the Contact Angle Test Method.

12. The topsheet of claim 1, wherein the second layer is substantially flat, wherein a contact angle on the land areas of the second layer between the plurality of the apertures is more than 70°, according to the Contact Angle Test Method.

13. The topsheet of claim 1, wherein the second layer comprises a plurality of protrusions, wherein the plurality of protrusions impart a three-dimensional shape to the second layer, wherein the plurality of protrusions of the first layer are at least partially aligned with the plurality of protrusions of the second layer, and wherein a contact angle on the land areas of the second layer between the plurality of the apertures is less than or equal to 70°, according to the Contact Angle Test Method.

14. The topsheet of claim 1, wherein the second layer comprises a plurality of protrusions, wherein the plurality of protrusions impart a three-dimensional shape to the second layer, wherein the plurality of protrusions of the first layer are aligned with the plurality of protrusions of the second layer, and wherein a contact angle on the land areas of the second layer between the plurality of the apertures is more than 70°, according to the Contact Angle Test Method.

15. The topsheet of claim 1, wherein the first layer is attached to the second layer in bonding areas by hot melt adhesive, and wherein the hot melt adhesive is hydrophilic.

16. The topsheet of claim 1, wherein the first layer is a nonwoven layer comprising a carrier web and a web comprising natural fibers, with part of the web comprising the natural fibers entering the carrier web.

17. The topsheet of claim 1, wherein the natural fibers are cotton fibers, bamboo fibers, or a mixture thereof.

18. An absorbent article comprising:
a longitudinal centerline;
a transversal centerline perpendicular to the longitudinal centerline;
the topsheet of claim 1;
a backsheet; and
an absorbent core positioned at least partially intermediate the backsheet and the topsheet.

19. A topsheet for use in an absorbent article having at least a first layer, wherein the first layer comprises at least 80% by weight of natural fibers by total weight of the first layer;
wherein the first layer comprises from 5% to 40% by weight of hydrophilic fibers selected from the group of synthetic fibers, natural fibers or combinations thereof, and from 60% to 95% by weight of hydrophobic natural fibers by total weight of the first layer; and
wherein the topsheet has a run-off of less than 40%, according to a Run-off Test Method described herein;
wherein the first layer has a plurality of apertures; and
wherein a contact angle on the plurality of the apertures is less than or equal to 70°, according to the Contact Angle Test Method;
wherein the first layer comprises a plurality of protrusions, wherein the plurality of protrusions impart a three-dimensional shape to the first layer, and wherein the plurality of the apertures are located between the plurality of the protrusions;

wherein the topsheet comprises a second layer in a face to face relationship with the first layer, and wherein the first layer and the second layer are in contact with each other between the plurality of the protrusions;

wherein the second layer has a plurality of apertures at least partially aligned with the plurality of apertures of the first layer;

wherein the first layer at least partially penetrates the second layer of the topsheet at the plurality of the apertures;

wherein the second layer comprises land areas between the plurality of the apertures; and wherein the second layer comprises synthetic fibers, natural fibers or combinations thereof.

* * * * *